United States Patent
Reichert

(12) 
(10) Patent No.: US 6,728,684 B1
(45) Date of Patent: Apr. 27, 2004

(54) ON-LINE PHARMACY AUTOMATED REFILL SYSTEM

(76) Inventor: Richard W. Reichert, 4011 Joshua La., Dallas, TX (US) 75287

( * ) Notice: Subject to any disclaimer, the term of this patent is extended or adjusted under 35 U.S.C. 154(b) by 0 days.

(21) Appl. No.: 09/398,131

(22) Filed: Sep. 17, 1999

Related U.S. Application Data

(63) Continuation of application No. 08/961,652, filed on Oct. 31, 1997, now Pat. No. 5,970,462.

(51) Int. Cl.[7] ............................................. G06F 17/60
(52) U.S. Cl. ........................................................ 705/2
(58) Field of Search ......................... 705/2, 3; 235/375; 700/216; 600/300

(56) References Cited

U.S. PATENT DOCUMENTS

| | | | |
|---|---|---|---|
| 4,766,542 A | * 8/1988 | Pilarczyk ........................ 705/3 |
| 5,070,452 A | 12/1991 | Doyle, Jr. et al. ........... 364/401 |
| 5,148,474 A | 9/1992 | Haralambopoulos et al. ............................ 379/111 |
| 5,208,762 A | 5/1993 | Charhut et al. .............. 364/478 |
| 5,500,890 A | 3/1996 | Rogge et al. .................. 379/91 |
| 5,737,396 A | * 4/1998 | Garcia ..................... 379/88.16 |
| 5,742,674 A | 4/1998 | Jain et al. .................... 379/209 |
| 5,845,255 A | * 12/1998 | Mayaud ........................... 705/3 |

FOREIGN PATENT DOCUMENTS

WO    WO 95/29455    * 11/1995

OTHER PUBLICATIONS

Bush, Anne; Technology turns the local corner drugstore into national pharmacy; Feb. 1995; Automatic I.D. News, p1; Dialog copy pp. 1–2.*

* cited by examiner

*Primary Examiner*—Thomas A. Dixon
(74) *Attorney, Agent, or Firm*—Head, Johnson & Kachigian

(57) ABSTRACT

An interative computer request processing system. In the preferred embodiment, the request processing system utilizes telephone and computer equipment to accept refill requests for patient prescriptions. The system receives information from a patient and performs prescription inquiries to a databank to determine patient information such as the status of prescriptions. The system remains operational whether or not interactive communications can be achieved with the databank. If communications are not available, the system stores the patient information. Therefore, the system always appears to the caller to be fully operational regardless of whether interactive communications are available. When communications are re-established, the databank and prescription inquiries are conducted, whereby the system validates or invalidates requests based on specified criteria. In a preferred embodiment, the system automatically attempts to notify a patient that the patient's request is invalid, thereby alerting the patient that the patient's prescription has not been filled.

14 Claims, 25 Drawing Sheets

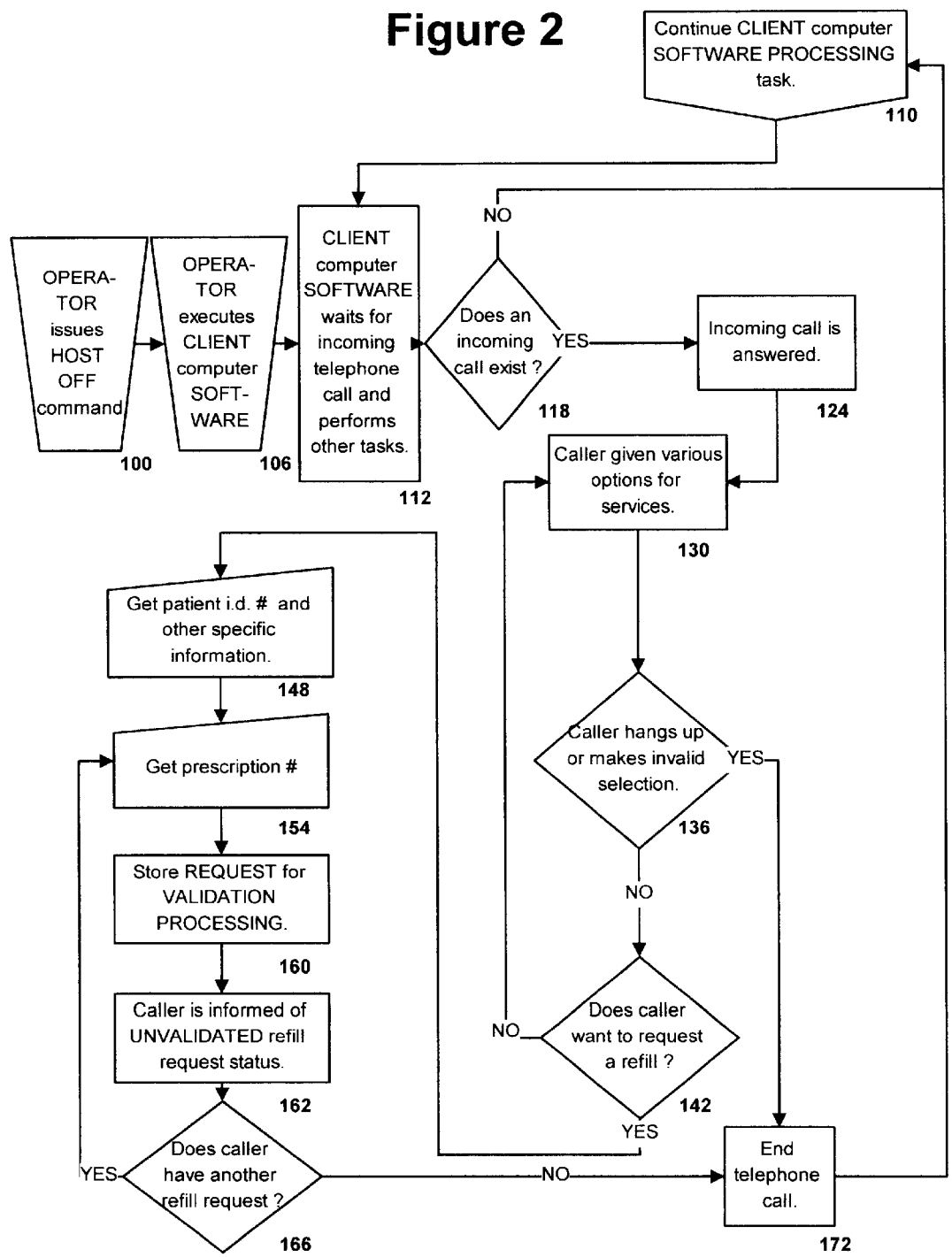

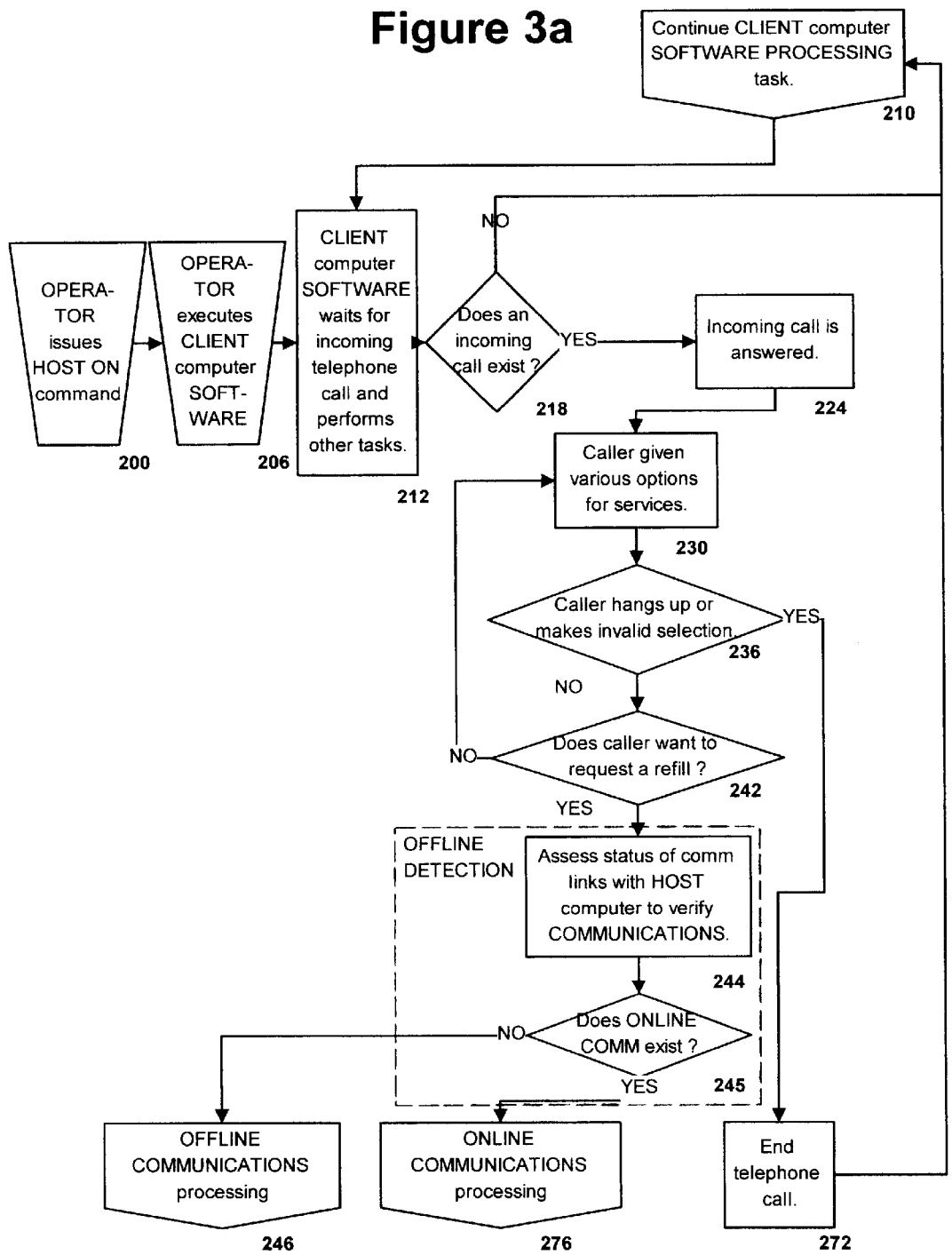

Figure 7a

CLIENT COMPUTER CONFIGURED FOR ON-LINE COMMUNICATIONS

*ISSUING* HOST ON command by OPERATOR.

*EXECUTING* SOFTWARE on CLIENT computer.

<u>*WAITING* for incoming telephone call</u>

0 *IF*    INCOMING CALL available
0 *THEN*
       *ANSWERING* incoming telephone call.
       *PLAYING* options for services to caller.
       *SELECTING* service option by caller.
       *REQUESTING* prescription refill service by caller.
       *ASSESSING* status of ON-LINE COMMUNICATIONS with HOST
          computer.

<u>*CAPTURING REQUESTS* from caller</u>

1 *IF*    ON-LINE COMMUNICATIONS available
       1 *THEN*
              *CAPTURE* REQUEST from caller.
              *VALIDATE* REQUEST on HOST computer.

2 *IF*    REQUEST is VALID
              2 *THEN*
                    *STORE* VALID REQUEST for
                          DISPENSE PROCESSING.
                   *INFORM* caller of VALIDATED status.
              2 *ELSE*
              2 *IF*    REQUEST is NOT VALID
              2 *THEN*
                   *INFORM* caller of VALIDATED status.
       1 *ELSE*
       1 *IF*    ON-LINE COMMUNICATIONS are not available
       1 *THEN*
              *CAPTURE* REQUEST from caller.
              *STORE* REQUEST for VALIDATION PROCESSING.
              *INFORM* caller of UNVALIDATED status.

(continued on figure 7b)

Flow Charts - Figures 3a and 3b

Figure 7b

CLIENT COMPUTER CONFIGURED FOR ON-LINE COMMUNICATIONS

(continued from figure 7a)

*ASK* caller if another REQUEST is desired.

1 *IF*    Another REQUEST is desired
   1 *THEN*
        Go to "<u>*CAPTURING REQUESTS* from caller</u>"
   1 *ELSE*
        End telephone call.
        Go to "<u>*WAITING* for incoming telephone call</u>"
0 *ELSE*
        Go to "<u>*WAITING* for incoming telephone call</u>"

Flow Charts - Figures 3a and 3b

Figure 8

CLIENT COMPUTER CONFIGURED FOR OFF-LINE COMMUNICATIONS

*ISSUING* HOST OFF command by OPERATOR.

*EXECUTING* SOFTWARE on CLIENT computer.

<u>*WAITING* for incoming telephone call</u>

0 *IF*    INCOMING CALL available
0 *THEN*
       *ANSWERING* incoming telephone call.
       *PLAYING* options for services to caller.
       *SELECTING* service option by caller.
       *REQUESTING* prescription refill service by caller.

<u>*CAPTURING REQUESTS* from caller</u>

*CAPTURE* REQUEST from caller.
       *STORE* REQUEST for VALIDATION PROCESSING.
       *INFORM* caller of UNVALIDATED status.

*ASK* caller if another REQUEST is desired.

1 *IF*    Another REQUEST is desired
       1 *THEN*
              Go to "<u>*CAPTURING REQUESTS* from caller</u>"
       1 *ELSE*
              End telephone call.
              Go to "<u>*WAITING* for incoming telephone call</u>"
0 *ELSE*
       Go to "<u>*WAITING* for incoming telephone call</u>"

Flow Chart - Figure 2

Figure 9a

CLIENT COMPUTER CONFIGURED FOR ON-LINE COMMUNICATIONS WITH AUTOMATIC VALIDATION AND NOTIFICATION PROCESSING

*ISSUING* HOST ON command by OPERATOR.

*EXECUTING* SOFTWARE on CLIENT computer.

<u>*WAITING* for incoming telephone call</u>

0 *IF*    INCOMING CALL available
    0 *THEN*
        *ANSWERING* incoming telephone call.
        *PLAYING* options for services to caller.
        *SELECTING* service option by caller.
        *REQUESTING* prescription refill service by caller.
        *ASSESSING* status of ON-LINE COMMUNICATIONS with HOST
            computer.

<u>*CAPTURING* REQUESTS from caller</u>

1 *IF*    ON-LINE COMMUNICATIONS available
    1 *THEN*
        *CAPTURE* REQUEST from caller.
        *PREPARE* REQUEST for INQUIRY TRANSACTION.
        *VALIDATE* REQUEST on HOST computer.

2 *IF*    REQUEST is VALID
        2 *THEN*
            *STORE* VALID REQUEST for DISPENSE
                PROCESSING.
            *INFORM* caller of VALIDATED status.
        2 *ELSE*
        2 *IF*    REQUEST is NOT VALID
        2 *THEN*
            *INFORM* caller of VALIDATED status.

1 *ELSE*

(continued on figure 9b)

Flow Charts - Figures 5a through 5e

Figure 9b

CLIENT COMPUTER CONFIGURED FOR ON-LINE COMMUNICATIONS WITH AUTOMATIC VALIDATION PROCESSING

(continued from figure 9a)

1 *IF*    ON-LINE COMMUNICATIONS are not available
1 *THEN*
      *CAPTURE* REQUEST from caller.
      *STORE* REQUEST for VALIDATION
          PROCESSING.
      *INFORM* caller of UNVALIDATED status.

*ASK* caller if another REQUEST is desired.

1 *IF*    Another REQUEST is desired
1 *THEN*
      Go to "<u>CAPTURING REQUESTS from caller</u>"
1 *ELSE*
      End telephone call.
0 *ELSE*
      End telephone call.

<u>*TESTING* for UNVALIDATED REQUESTS in need of VALIDATION PROCESSING.</u>

0 *IF*    A REQUEST exists
0 *THEN*
      *ACCESSING* status of ON-LINE COMMUNICATIONS with
          HOST computer.

1 *IF*    ON-LINE COMMUNICATIONS available
      1 *THEN*
          *RETRIEVE* REQUEST from storage.
          *PREPARE* REQUEST for INQUIRY TRANSACTION.
          *VALIDATE* REQUEST on HOST computer.

(continued on figure 9c)

Flow Charts - Figures 5a through 5e

Figure 9c

CLIENT COMPUTER CONFIGURED FOR ON-LINE COMMUNICATIONS WITH AUTOMATIC VALIDATION PROCESSING

(continued from figure 9b)

2 *IF*    REQUEST is VALID
    2 *THEN*
          *STORE* VALID REQUEST for
              DISPENSE PROCESSING.
    2 *ELSE*
          *STORE* INVALID REQUEST for
              NOTIFICATION PROCESSING.
  1 *ELSE*
  1 *IF*    ON-LINE COMMUNICATIONS are not available
  1 *THEN*
        End VALIDATION PROCESSING.
0 *ELSE*
      End VALIDATION PROCESSING.

*TESTING* for INVALID REQUESTS in need of NOTIFICATION
      PROCESSING.

0 *IF*    Notification time is within allowable calling time window
0 *THEN*
    1 *IF*    A REQUEST exists
    1 *THEN*
          *RETRIEVE* INVALID REQUEST from storage.
          EXTRACT telephone number, VALIDATED status,
              original request time, and retry count from
              REQUEST.
          *PERFORM* NOTIFICATION telephone call with VALIDATED
              status informational MESSAGE.

2 *IF*    MESSAGE was DELIVERED
        2 *THEN*
              *INCREMENT* message delivery attempt counter.
              *STORE* message DELIVERED status for
                  REPORT PROCESSING.
        2 *ELSE*

(continued on figure 9d)

Flow Charts - Figures 5a through 5e

Figure 9d

CLIENT COMPUTER CONFIGURED FOR ON-LINE COMMUNICATIONS WITH AUTOMATIC VALIDATION PROCESSING

(continued from figure 9c)

2 *IF*     MESSAGE is DELIVERABLE
2 *THEN*
         *INCREMENT* message delivery attempt counter.
         *STORE* message NOT DELIVERED status for
             future NOTIFICATION PROCESSING.

2 *ELSE*
         *INCREMENT* message delivery attempt counter.
         *STORE* message NOT DELIVERABLE status for
             REPORT PROCESSING.
1 *ELSE*
         End NOTIFICATION PROCESSING.
0 *ELSE*
         End NOTIFICATION PROCESSING.

Flow Charts - Figures 5a through 5e

ON-LINE PHARMACY AUTOMATED REFILL SYSTEM

CROSS-REFERENCE OF RELATED APPLICATION

This application is a continuation application of Pending application Ser. No. 08/961,652, filed Oct. 31, 1997 now U.S. Pat. No. 5,970,462 entitled "On-line Pharmacy Automated Refill System".

REFERENCE TO MICROFICHE APPENDIX

This application is not referenced in any microfiche appendix.

BACKGROUND OF THE INVENTION

1. Field of the Invention

This invention is directed to an interactive computer request processing system. More particularly, the invention relates to the field of refilling patient prescriptions using telephone and computer equipment even if patient databank computer interactive communications are unavailable.

2. Background Art

Patients require health care services, such as prescription refills, from health care service provider organizations, such as pharmacies. These organizations often provide automated services to their patients to increase efficiency. Consequently, automated pharmacy technologies must be developed and advanced to provide such services. The resulting technology has become increasingly complex. Multiple layers of automated computer equipment are being placed between a patient and the health care provider's service. Therefore, multiple points of failure in such technology exist. Any point of failure can cause an automated system, such as an automated pharmacy prescription refill system, to be unavailable for use by a patient demanding the service if some component of the automated system has failed.

Existing automated pharmacy refill systems utilize an answering device to interact with a databank. The databank contains specific patient information including the status of prescriptions. A difficulty with such systems is that if the databank is unavailable to the answering device, the answering device is unable to perform prescription inquiries for the patient until such time as communication with the databank is re-established. If the patient databank computer's interactive communications are unavailable to the answering computer, the answering computer cannot perform prescription inquiries on demand for the patients since it requires interactive communication with the patient databank computer. Typically, when encountering this situation, callers are informed that services are unavailable. A caller must, therefore, end the call without being provided the needed service.

SUMMARY OF THE INVENTION

Consequently, the primary objective of this invention is to allow a patient to request prescription refills on a client computer or answering computer regardless of whether interactive communications are possible with the patient databank computer. Interactive communications with the patient databank computer typically perform prescription refill inquiries and subsequent interpretation of an inquiry response. If the patient databank computer is unavailable, the client or answering computer accepts and stores patient refill requests until interactive communications with the patient databank computer are available. When interactive communications are re-established, the client computer retrieves refill requests from the local database and transmits inquiries to the patient databank computer for validation. The host computer checks each refill request to determine if the refill request is valid, i.e., if it is valid to refill the prescription. If the prescription is still active, the last fill date, the days supply and the grace period are used to determine when the prescription can be filled.

The invention presented herein is a means for allowing patients to request their prescription refills on demand even if the patient databank computer is unavailable for interactive communications with the client computer at the moment in time when the inquiry needs to be made. The invention consists of specific computer programming software algorithms and techniques, and also specific defined procedures performed by computer operators, which operate on a general purpose computer engineered and programmed for answering incoming telephone calls and performing pharmacy prescription refill processing.

More particularly, the invention enables patients using an ordinary telephone to place a telephone call that is answered by a client computer. The client computer collects from the calling patient specific information necessary to refill the patient's prescription, preferably by touch-tone input from the patient's phone. The client computer has interactive communications with a patient databank computer that contains specific patient information including the status of prescriptions. The client computer, using the collected patient information, queries the patient databank computer. The patient databank computer then returns a response with particular information about the patient's prescription. The information is then interpreted and the client computer informs the patient whether or not the prescription can be refilled. However, if the interactive communications link with the patient databank computer is unavailable, then the client computer collects the calling patient's specific information for future validation processing. The client computer then informs the patient that if the prescription refill is valid, the prescription will be available to the patient at some point in time.

In one embodiment of the invention, the client computer notifies the patient of the patient's refill status once interactive communications with the host computer have been re-established and the patient's request has been validated. In the notification step, the client computer extracts the telephone number and status associated with the request and attempts to contact the patient. The client computer then states whether the call was delivered for later reporting to an operator.

BRIEF DESCRIPTION OF THE DRAWINGS

FIGS. 3a and 3b are flow diagrams depicting the on-line communications configuration of the client computer.

FIGS. 7a and 7b are summaries of the program used by the client computer when configured for on-line communications.

FIG. 8 is a summary of the program used by the client computer when configured for off-line communications.

FIGS. 9a, 9b, 9c and 9d are summaries of the program used by the client computer when configured for on-line communications with automatic validation and notification processing.

DETAILED DESCRIPTION OF THE PREFERRED EMBODIMENTS

Before explaining the invention in detail, it is to be understood that the invention is not limited in its application to the specific details of the implementation of the software as used for automated prescription refill systems outlined in the following descriptions and charts. The invention is capable of other embodiments and of being practiced or carried out in many ways. It is understood that the phraseology and terminology employed herein is for the purpose of description and not limitation.

Figure 1:
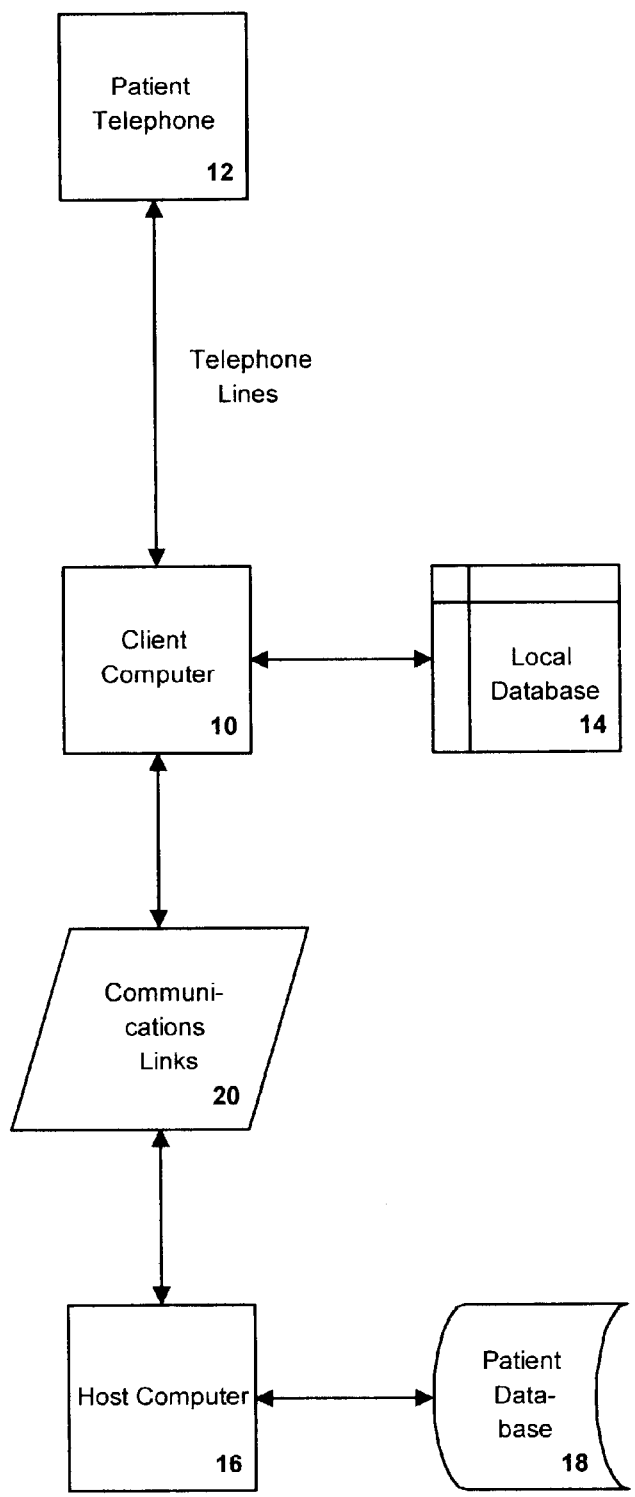
FIG. 1 depicts the on-line pharmacy automated refill system of the present invention.

Referring to FIG. 1, the answering computer or client computer 10 is designed to answer incoming telephone calls from patient telephone 12 and accept information from patients. Client computer 10 uses a complex software program that executes during normal operations. The information is stored in data storage 14 for use in processing prescription refill requests. The patient databank computer or host computer 16 contains patient databank 18, which contains specific patient information, including the patient's prescription information. Client computer 10 and host computer 16 are interconnected using one or more communications links 20 that support interactive communications between the computers. Examples of communication links 20 that may be used include serial connections such as VT100s and VT320s for connecting a dumb terminal to a mainframe, but other means, such as LAN connections, may be used to communicate with host computer 16. It is noted that processes performed by client computer 10 are in theory parallel processes and not serial processes in spite of computer operating system functional limitations.

Interactive communications between client computer 10 and host computer 16 consist of defined messages that are sent and received between the computers. In general, client computer 10 sends a message (initiates a transaction) to host computer 16 and host computer 16 sends a message (completes a transaction) back to client computer 10. The sending and receiving of a defined set of messages will be referred to as a transaction. A transaction is initiated by client computer 10 which sends a defined initiator message to host computer 16. Host computer 16 responds predictably with respect to the particular initiator message by sending a defined response message back to client computer 10, thus completing the transaction.

In practice, client computer 10 preferably uses a specific initiator message to test the current interactive communications status with host computer 16 and also a specific initiator message to make prescription refill request inquiries. Host computer 16 sends specific response messages with respect to the specific initiator messages back to client computer 10 so that appropriate actions can be taken, such as informing the calling patient of his or her prescription status. If no response message is received by client computer 10 after an initiator message has been sent, interactive communications between host computer 16 and client computer 10 have been interrupted. Additionally, if a "hardware status" such as a phone dial tone or other "hardware status" has been interrupted, then interactive communications between host computer 16 and client computer 10 have been interrupted. Client computer 10 will then assume that interactive communications are not available. Therefore, any attempts by client computer 10 to initiate a transaction with host computer 16 to determine if host computer 16 will respond appropriately for re-establishing interactive communications will be automatically suspended.

Interactive communications between client computer 10 and host computer 16 can be activated (on-line mode) or deactivated (off-line mode) by either client computer 10 or host computer 16.

When client computer 10 engages in interactive communications with host computer 16, client computer 10 is considered to be on-line with host computer 16. Conversely, when there is no interactive communication, client computer 10 is considered to be off-line from host computer 16.

An automated prescription refill system consists primarily of client computer 10 and host computer 16. Client computer 10 answers incoming telephone lines and interacts with patients over the telephone. Host computer 16 contains the patient information databank or patient database 18 and provides practically instantaneous information to client computer 10 using one or more interactive communication links that support the interactive communications, which consist of specific transactions. Client computer 10 possesses automated refill system software, known in the art, that causes client computer 10 to answer incoming telephone lines, interact with patients over the telephone to collect specific information, and manage interactive communications with host computer 16.

For interactive communications to occur between client computer 10 and host computer 16, host computer 16 must be operational and permit client computer 10 access. Client computer 10 does not control the on-line or off-line interactive communications capabilities of host computer 16, but can determine if interactive communications are on-line or off-line. In practice, the interactive communications capabilities of host computer 16 may not be available to client computer 10 for a variety of reasons. For example, a system operator of host computer 16 may be performing maintenance work, electrical storms may be disrupting communications links, power failures may occur, etc. During such times, client computer 10 has the capability to operate autonomously without interactive communications with host computer 16 by storing patient data such as patient identification numbers and prescription numbers. The patient is thus informed of the unvalidated refill request status.

In one embodiment, after communications have been re-established between client computer 10 and host computer 16 and a prescription request has been validated, client computer 10 performs a notification telephone call to the patient to inform the patient of the request status.

It is noted that, for the purposes of this application, "operator" is any entity capable of issuing a command, including humans, software processes, hardware processes, and other means.

Client computer 10 can automatically detect interactive communications loss (off-line detection) with host computer 16 without human intervention from a computer operator. Also, an operator can manually put communications off-line by issuing a command to client computer 10. Conversely, the operator can manually put communications on-line by issuing a command to client computer 10.

A software command referred to as the "host off command" can be issued by an operator. The "host off command" configures client computer 10 to operate with the assumption that interactive communications with host computer 16 are unavailable. Client computer 10 then functions according to the configuration and does not expect nor require interactive communications with host computer 16 to exist.

A software command referred to as the "host on command" can be issued by an operator. The "host on command" configures client computer 10 to operate with the assumption that interactive communications with host computer 16 are available. Client computer 10 then functions according to the configuration and does expect but does not require interactive communications with host computer 16 to exist.

Operator Specified Off-line Communications Scenario

Figure 5A:
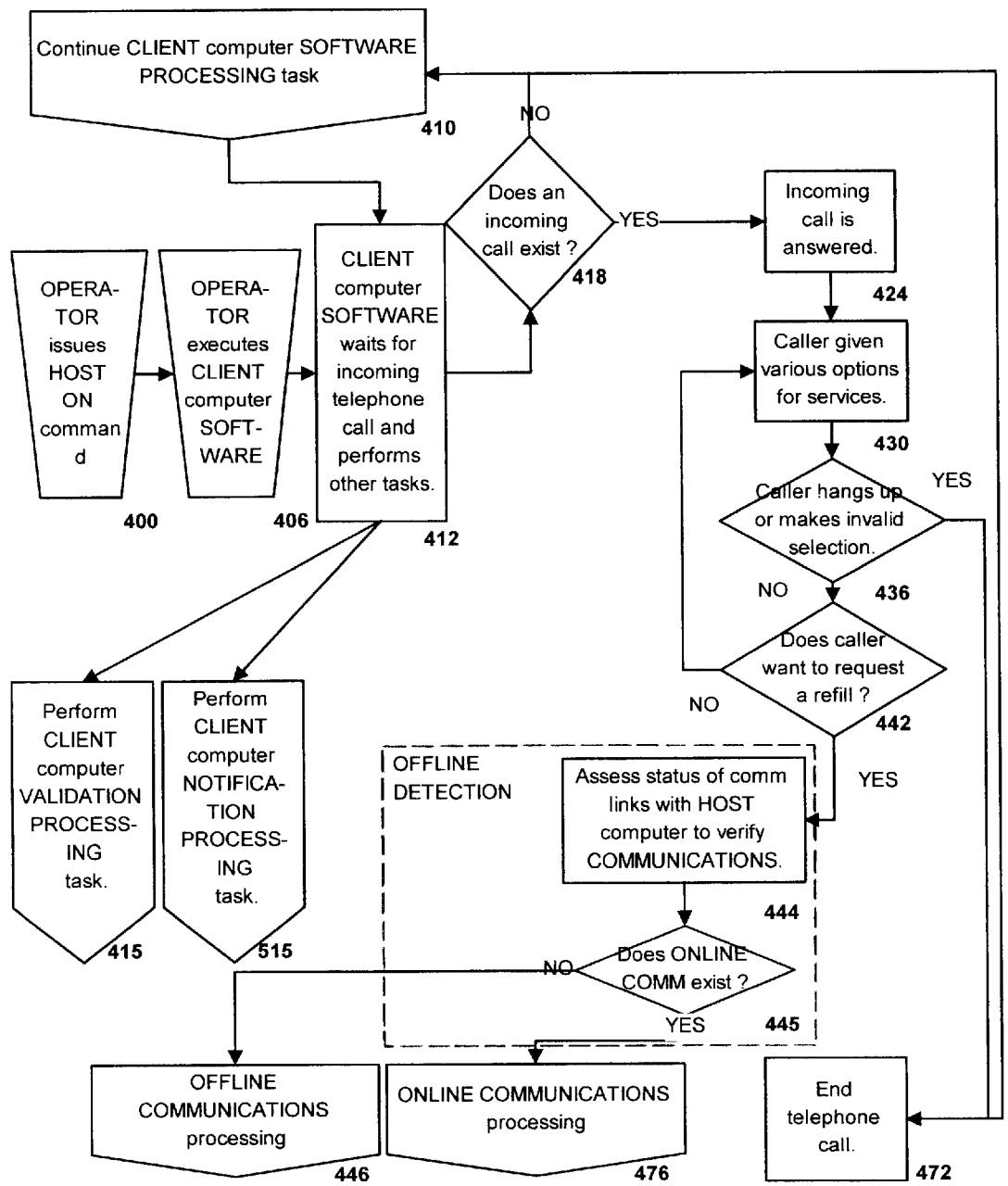
FIGS. 5a, 5b, 5c, 5d and 5e are flow diagrams depicting the on-line communications configuration of the client computer with automatic validation and notification processing.
Figure 5B:
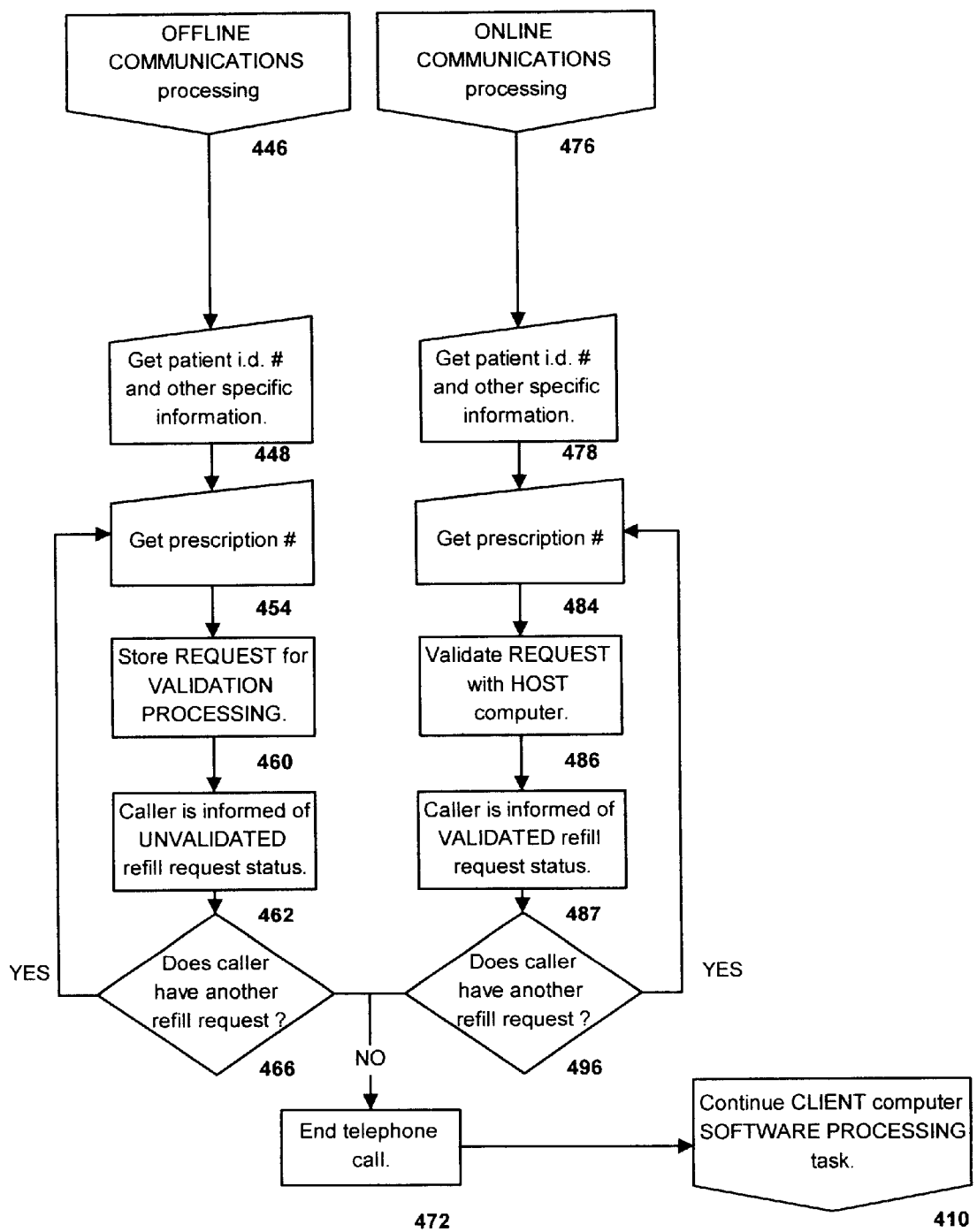
Figure 5C:
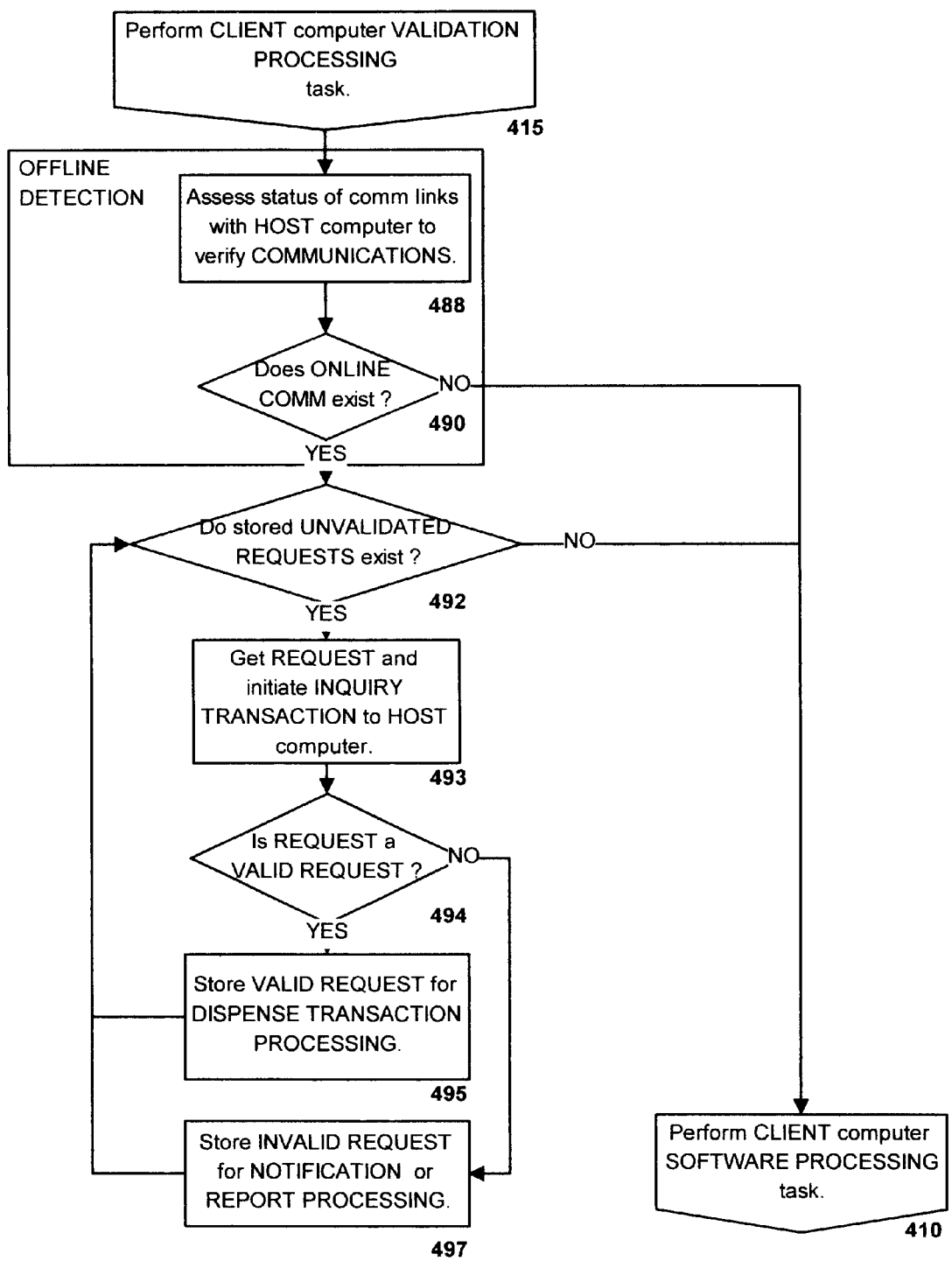
Figure 5D:
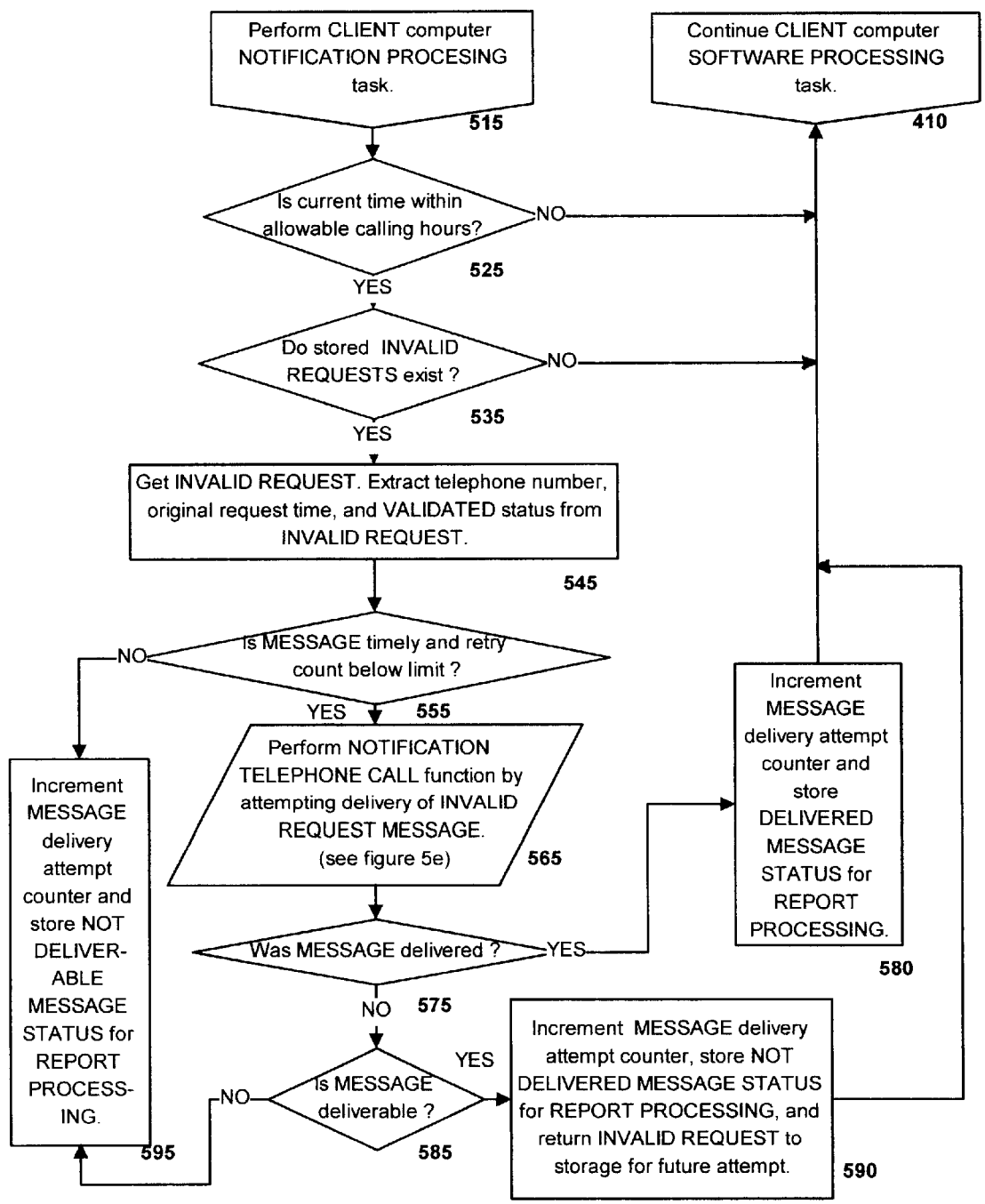
Figure 5E:
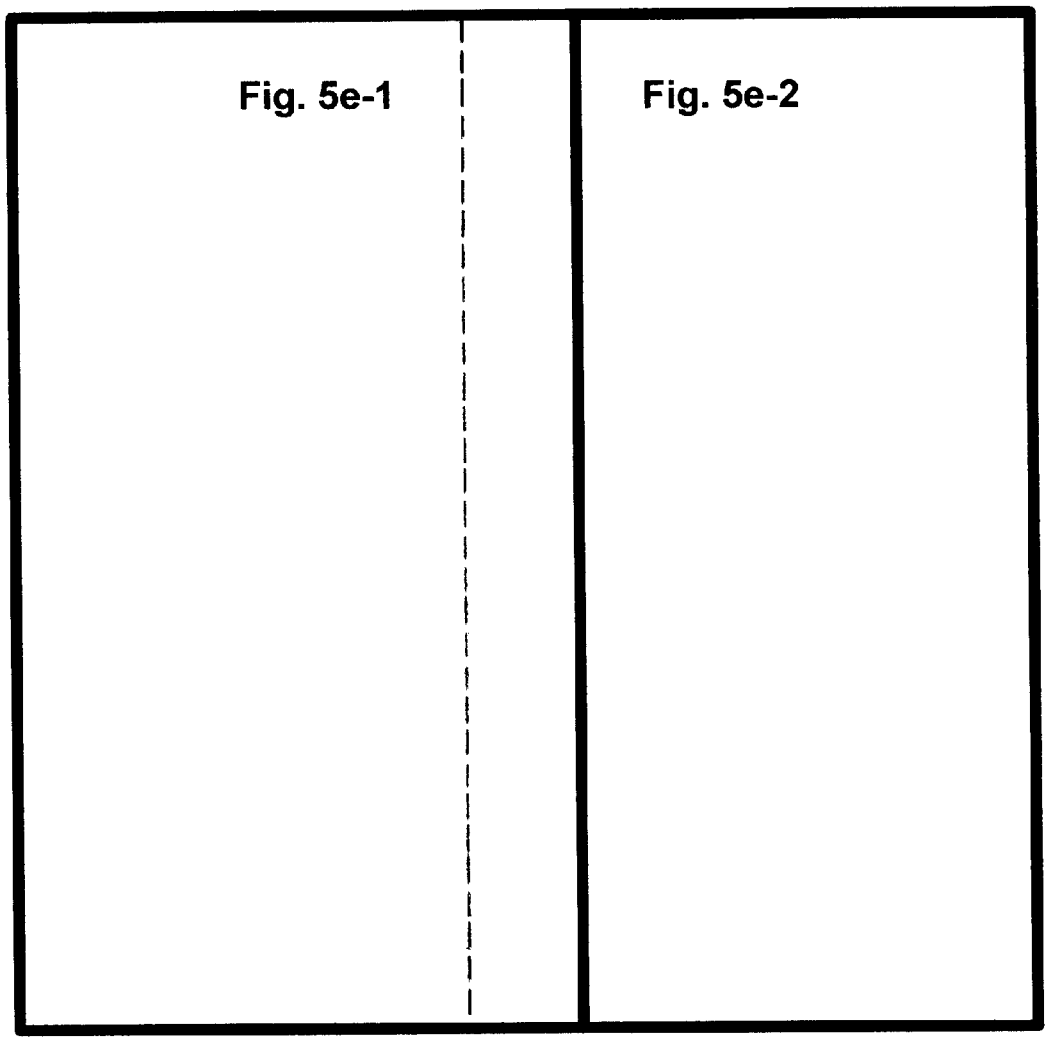
Figures 1, 5E:
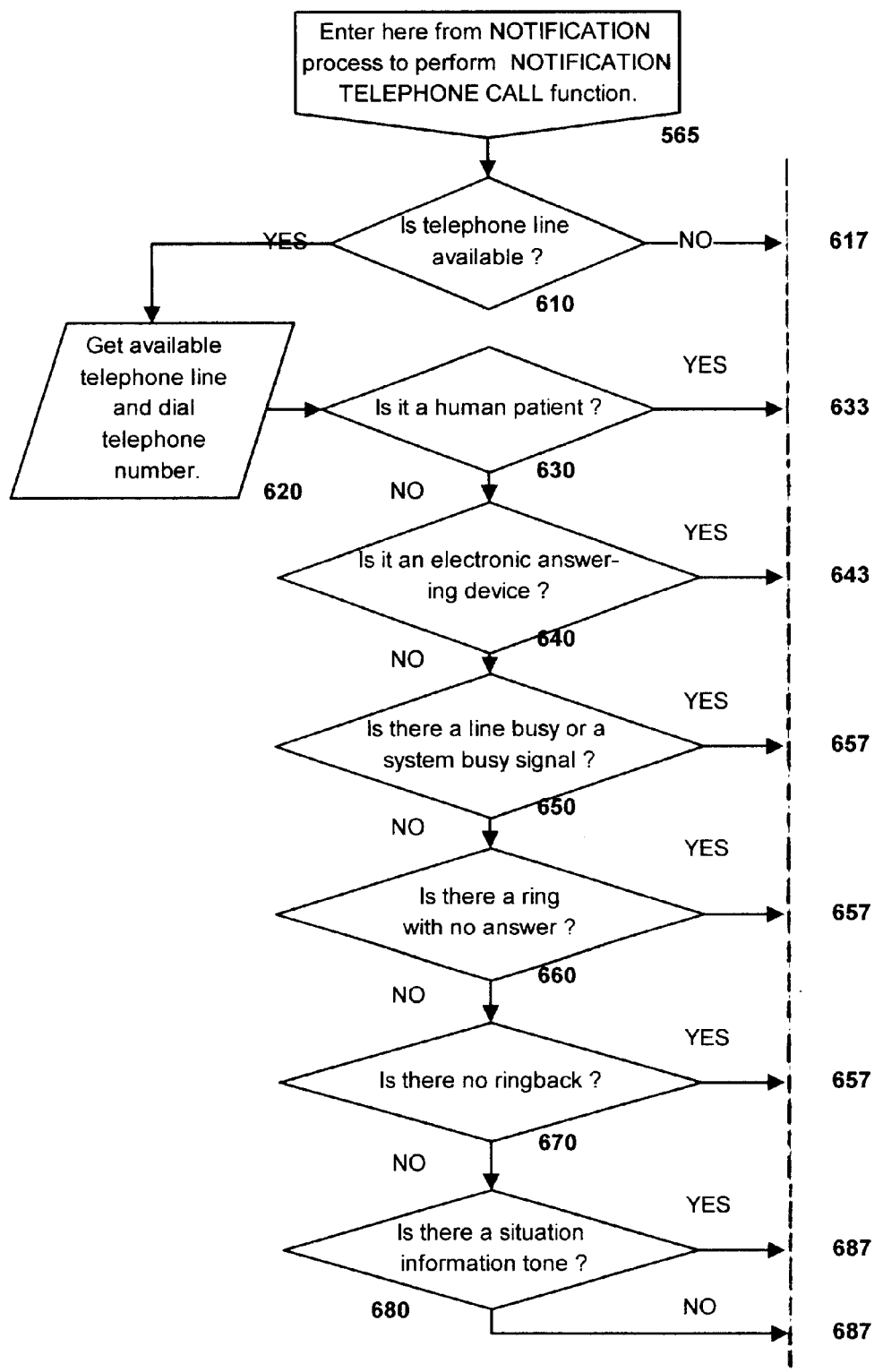
Figures 2, 5E:
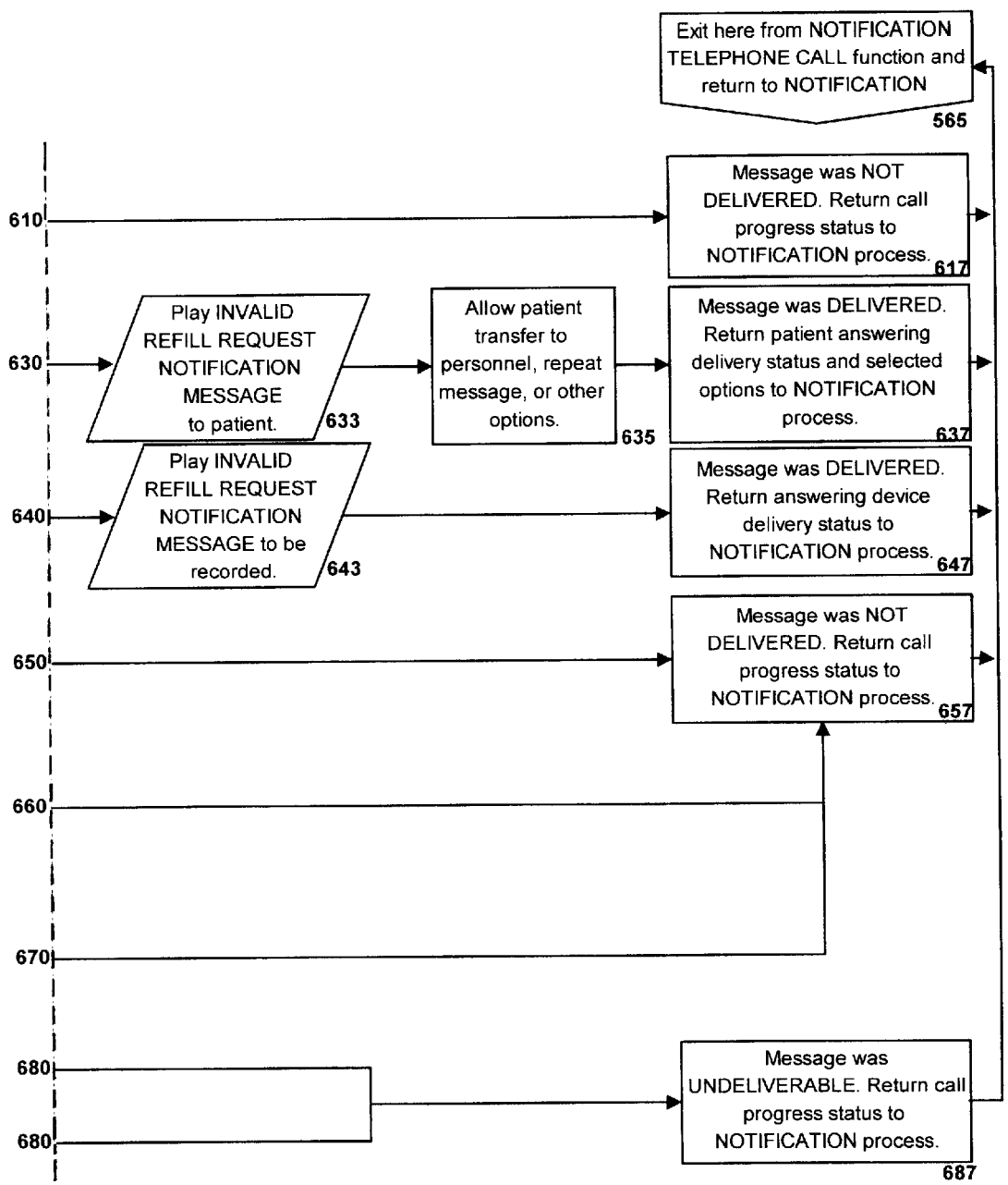
FIG. 2 is a flow diagram depicting the off-line communications configuration of the client computer.

Referring now to FIG. 2, when client computer 10 is taken off-line from host computer 16 by an operator using the "host off command", represented by box 100, client computer 10 is configured for off-line communications. The "host off command" executes a simple software program that sets configuration files to be read by client computer 10. The operator must then execute the software of client computer 10, represented by box 106. Client computer 10 uses software to check for incoming telephone calls and perform other tasks as represented by boxes 112 and 118. Client computer 10 answers incoming calls, represented by box 124, and gives the caller various options for services, represented by box 130, thereby continuing to collect specific request information from the patient. Examples of various options for services include pharmacy hours of operation and location, information on medications, numbers to contact in case of questions or an option to transfer to a live person. Client computer 10 then determines whether the caller has ended the telephone call or made an invalid selection as represented by box 136. If so, client computer 10 ends the telephone call as represented by box 172. Otherwise, client computer 10 queries whether the caller wants to request a refill, as represented by box 142. The specific request information preferably consists of, but is not limited to: a variable length patient identification number, represented by box 148; a variable length prescription number, represented by box 154; and, optionally, a variable length telephone number, credit card number or other information. The specific request information is stored locally in data storage 14 of client computer 10.

Client computer 10 gives the outward seamless appearance to the patient that the refill system is fully operational. This appearance is maintained even though interactive communications between client computer 10 and host computer 16 are not available for patient refill request inquiry transactions. The request information is stored on local database 14 of client computer 10 for future prescription refill validation processing, as represented by box 160. The caller is then informed of his or her unvalidated status, as represented by box 162. "Unvalidated status" means that the prescription request has been accepted pending validation and will be processed if the request is found to be valid during validation processing. Prescription refill validation processing with host computer 16 will take place when on-line communications become available. After stored unvalidated refill requests are processed by either manual or automatic validation processing, refill requests determined to be valid are dispensed, whereas refill requests determined to be invalid are not dispensed, but are stored for notification processing. Both valid and invalid refill requests are considered to be validated, as opposed to unvalidated, after the validation process has been performed.

Finally, client computer 10 queries the caller whether the caller has another refill request as represented by box 166. If so, client computer 10 will then obtain a new prescription number from the client as represented by box 154; otherwise, client computer 10 ends the telephone call as represented by box 172.

Operator Specified On-line Communications with Off-line Detection Scenario

Referring now to FIG. 3a, to place client computer 10 on-line, an operator issues the "host on command", represented by box 200. The operator must then execute the software of client computer 10, represented by box 206. The "host on command" executes a simple software program that sets configuration files to be read by client computer 10. Client computer 10 checks for incoming telephone calls and performs other tasks as represented by boxes 212 and 218. Client computer 10 answers incoming calls, represented by box 224, and gives the caller various options for services, represented by box 230, thereby continuing to collect specific request information from the patient.

Client computer 10 determines whether the caller has ended the telephone call or made an invalid selection as represented by box 236. If so, client computer 10 ends the telephone call as represented by box 272. Otherwise, client computer 10 queries whether the caller wants to request a refill as represented by box 242.

When client computer 10 is on-line with host computer 16 and a patient calls client computer 10 and requests a prescription refill, client computer 10 performs off-line detection by using a verification transaction, a software method, or by monitoring statuses rendered from other communications-related hardware devices, as represented by box 244. The verification transaction immediately determines, as represented by box 245, whether interactive communications with host computer 16 are available to perform inquiries.

If interactive communications with host computer 16 are not available at that moment, i.e., host computer 16 is off-line, then off-line communications processing is initiated, represented by box 246. Once engaged in off-line communications processing, client computer 10 collects specific request information from the patient, represented by boxes 248 and 254, shown in FIG. 3b. The specific request information preferably consists of, but is not limited to: a variable length patient identification number, represented by box 248; a variable length prescription number, represented by box 254; and, optionally, a variable length telephone number, credit card number or other information. Local database 14 of client computer 10 then stores the caller's request, as represented by box 260, for validation processing when on-line communications with host computer 16 are restored. The caller is then informed of his or her unvalidated status, as represented by box 262. Preferably, client computer 10 informs the caller of the unvalidated refill status with a message similar to, "if your prescription request is valid, it will be filled". Finally, client computer 10 will query whether the caller has another refill request, as represented by box 266. If so, client computer 10 will then obtain a new prescription number from the client, as represented by box 254. Otherwise, client computer 10 ends the telephone call, as represented by box 272.

Figure 3B:
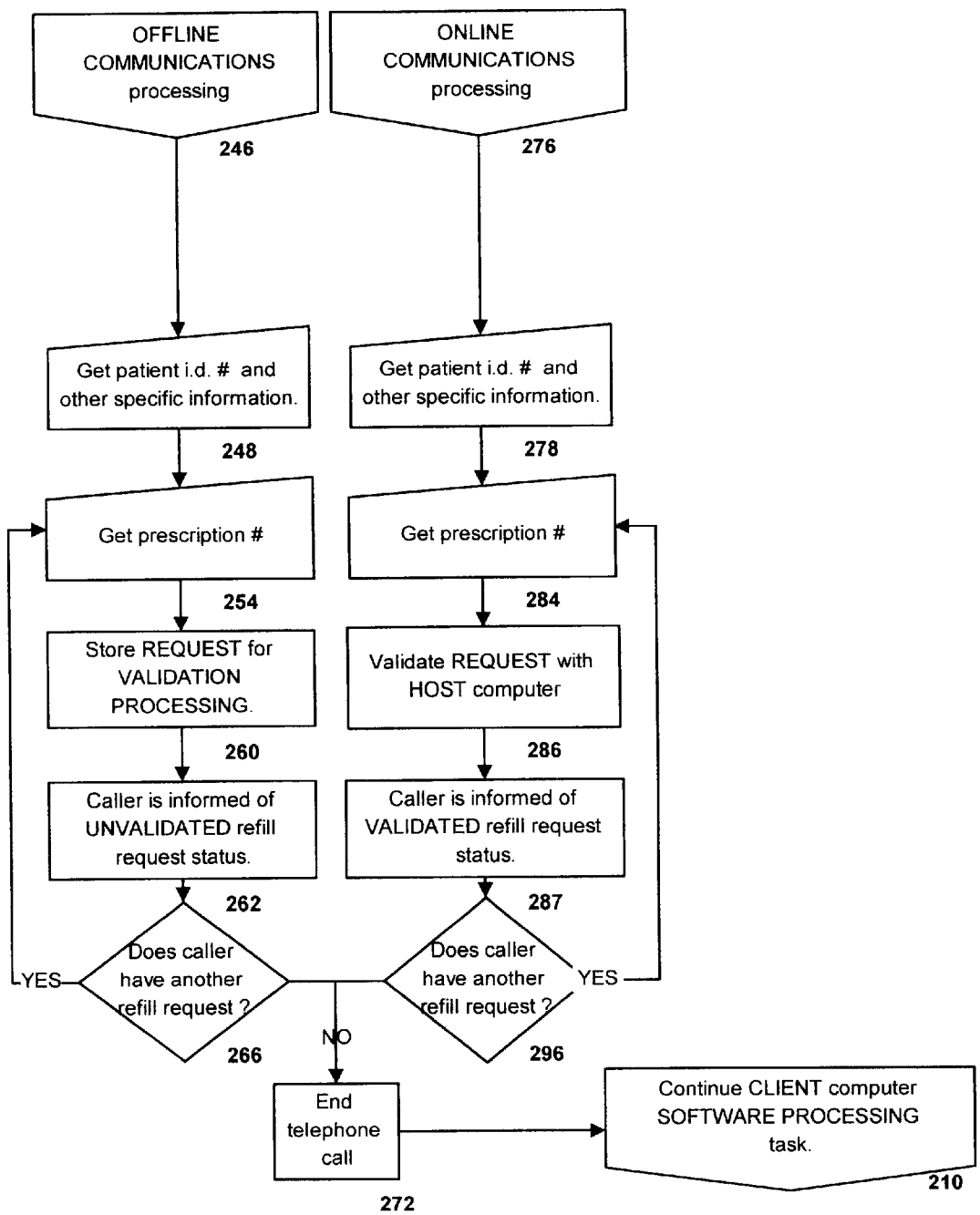

If client computer 10 determines, as represented by box 245 shown in FIG. 3a, that interactive communications with host computer 16 are available, then on-line communications processing is initiated, represented by box 276. Client computer 10 functions according to the on-line configuration and thus expects interactive on-line communications with host computer 16 to exist. Once engaged in on-line communications processing, client computer 10 collects specific request information from the patient, represented by boxes 278 and 284 shown in FIG. 3b. Client computer 10 then validates the caller's request with the host computer, as represented by box 286. The caller is then informed of his or her validated refill request status, as represented by box 287. Finally, client computer 10 will query the caller whether the caller has another refill request, as represented by box 296. If so, client computer 10 will then obtain a new prescription number from the client, as represented by box 284. Otherwise, client computer 10 ends the telephone call, as represented by box 272.

Validation Processing

Validation processing occurs manually or automatically at the discretion of the operator. Manual validation processing is performed by software commands issued by the operator. Automatic validation processing is performed automatically by a software process on client computer 10 when it is configured by the operator for on-line communications and automatic validation processing. To determine whether a refill request is valid, client computer 10 first determines whether the prescription is still valid. If the prescription is still valid, then the last fill date, the days supply and grace period are used to determine when the prescription can be filled. Manual and automatic validation processing is discussed in detail below.

Operator Initiated Validation Processing

Figure 4:
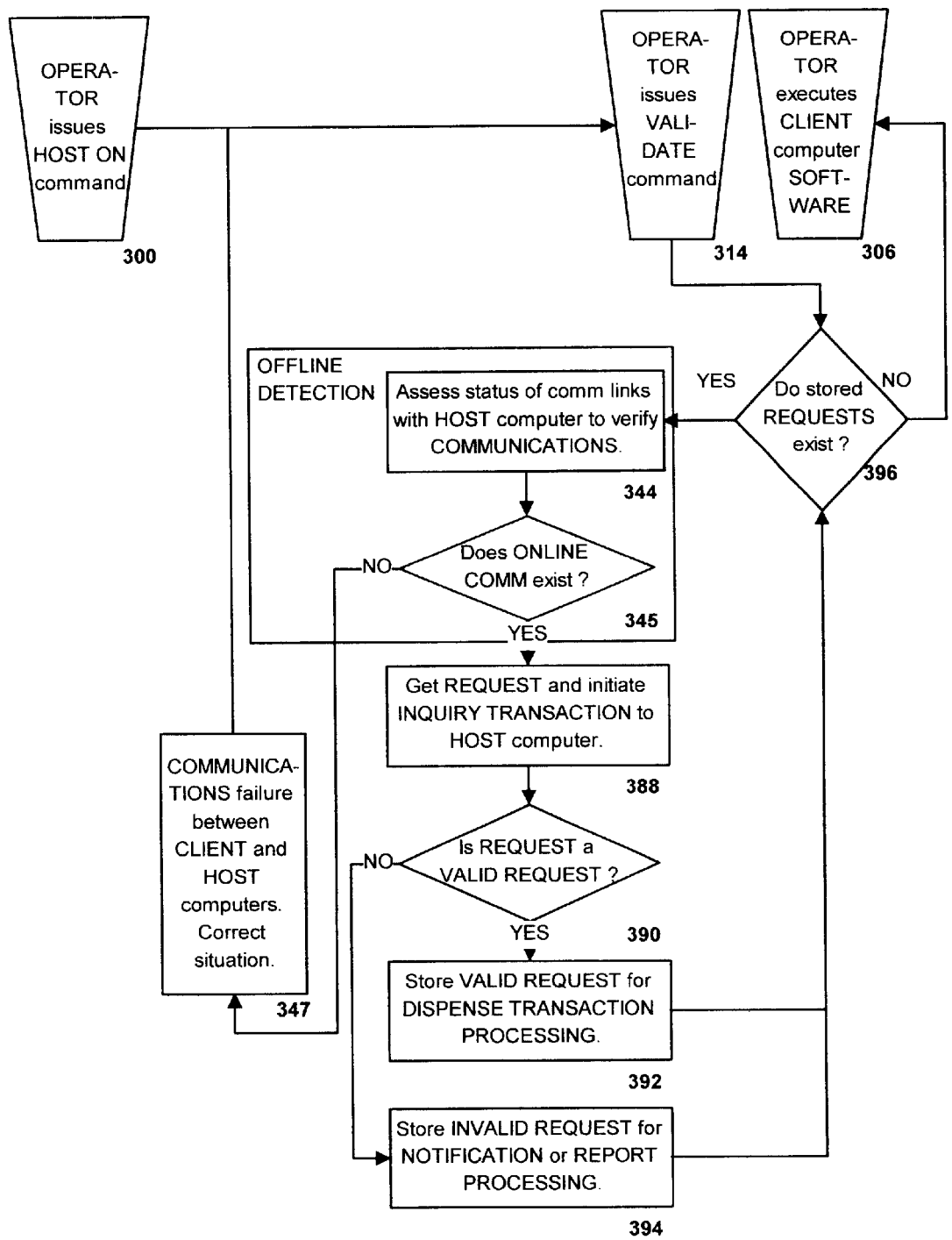
FIG. 4 is a flow diagram depicting the on-line communications configuration of the client computer with operator initiated validation processing.

When the operator has configured client computer 10 for off-line communications, then all requests are stored on client computer 10, as was discussed in reference to FIG. 2, wherein the procedure is represented by boxes 100–160. However, in order to perform validation processing, on-line communications must be available. Therefore, referring now to FIG. 4, the operator must configure the software using the "HOST ON" command for on-line communications, represented by box 300. A command referred to as the "VALIDATE command" is then issued by the operator, represented by box 314. The VALIDATE command utilizes a software program that client computer 10 executes during normal on-line operations, as discussed below.

The term "normal operations" refers to when client computer 10 is answering calls after the operator has either configured the client computer for on-line or off-line communications. The term "abnormal operations" refers to when on-line communications have been interrupted, off-line detection has occurred, and requests are being stored for validation processing. Validation processing is effected either manually using the VALIDATE command or automatically by software processes of the software program executing on client computer 10 when it is configured for on-line communications and configured for automatic validation processing.

Client computer 10 may be configured for off-line communications by the operator using the HOST-OFF command as discussed in reference to box 100, FIG. 2, or may be operated with off-line communications as the result of the off-line detection process as represented in boxes 245 and 246, in FIG. 3a.

The client computer may be configured for on-line communications by the operator using the HOST-ON command, as represented by box 300 and as discussed in reference to box 200, FIG. 3a. The operator may then issue the VALIDATE command as represented by box 314 to perform validation processing before executing client computer 10 operations as represented by box 306.

After the "VALIDATE command" is issued by the operator, client computer 10 determines, as represented by box 396, whether stored requests exist. If no stored requests exist, then the operator executes the software of client computer 10, represented by box 306.

If stored requests do exist, then when client computer 10 is on-line with host computer 16, client computer 10 performs off-line detection by using a verification transaction, a software method, or by monitoring statuses rendered from other communications-related hardware devices, as represented by box 344. The verification transaction determines, as represented by box 345, whether interactive communications with host computer 16 are available to perform inquiries.

If on-line communications with host computer 16 are not available, i.e., host computer 16 is off-line, then a communications failure between client computer 10 and host computer 16 exists. The operator is then notified of the communications failure between client computer 10 and host computer 16, as represented by box 347.

If client computer 10 determines, as represented by box 345, that interactive communications with host computer 16 are available, then a refill request inquiry transaction is initiated from client computer 10 to host computer 16, as represented by box 388.

Client computer 10 then determines, as represented by box 390, whether the client request is a valid request. A request that is validated by host computer 16 is stored on data storage 14 of client computer 10 as a valid pending refill request for dispense transaction processing, represented by box 392. Conversely, invalid refill requests are stored on client computer 10 as invalid refill requests for manual or automated notification or report processing, as represented by box 394. Valid refill requests are used in a dispense transaction to dispense the prescription refill on host computer 14. After valid or invalid refill requests are stored, as represented by boxes 392 and 394, client computer 10 then determines, as represented by box 396, whether any additional stored requests exist.

Automatic Validation Processing

It is noted that when the operator has configured the software of client computer 10 for on-line communications, as was discussed with reference to FIGS. 3a and 3b, wherein the procedure is represented by boxes 200–296, the requests are stored on data storage 14 of client computer 10, represented by box 260. Referring now to FIG. 5b, box 460 also represents the storage of requests on client computer 10. However, box 460 represents that the requests are stored for validation processing when off-line detection has occurred, as shown in FIG. 5b.

Referring now to FIG. 5a, in order to perform validation processing, on-line communications must be available. To place client computer 10 on-line, an operator issues the "host on command", represented by box 400. The operator preferably then executes the software of client computer 10, represented by box 406. The software of client computer 10 has preferably been configured to perform validation processing and notification processing. Client computer 10 checks for incoming telephone calls and performs other tasks as represented by boxes 412 and 418. Such tasks include performing client computer validation processing, as represented by box 415, discussed below, or client computer notification processing as represented by box 515, also discussed below. Client computer 10 answers incoming calls, represented by box 424, and gives the caller various options for services, represented by box 430, thereby continuing to collect specific request information from the patient such as patient identification, patient prescription number, or other information. Examples of various options for services include pharmacy hours of operation and location, information on medications, numbers to contact in case of questions, or an option to transfer to a live person.

Client computer 10 determines whether the caller has ended the telephone call or made an invalid selection as represented by box 436. If so, client computer 10 ends the telephone call as represented by box 472. Otherwise, client computer 10 queries whether the caller wants to request a refill as represented by box 442.

When client computer 10 is on-line with host computer 16 and a patient calls client computer 10 and requests a prescription refill, client computer 10 performs off-line detection by using a verification transaction, a software method, or by monitoring statuses rendered from other communications-related hardware devices, as represented by box 444. The verification transaction determines, as represented by box 445, whether interactive communications with host computer 16 are available to perform inquiries.

If interactive communications with host computer 16 are not available at that moment, i.e., host computer 16 is off-line, then off-line communications processing is initiated, represented by box 446. Once engaged in off-line communications processing, client computer 10 collects specific request information from the patient, represented by boxes 448 and 454 shown on FIG. 5*b*. The specific request information preferably consists of, but is not limited to: a variable length patient identification number, represented by box 448; a variable length prescription number, represented by box 454; and, optionally, a variable length telephone number, credit card number or other information. Client computer 10 then stores the caller's request on local database 14, as represented by box 460, for validation processing when on-line communications with host computer 16 are restored. The caller is then informed of his or her unvalidated refill request status, as represented by box 462, with a message similar to, "if your request is valid, it will be filled". Finally, client computer 10 will query whether the caller has another refill request, as represented by box 466. If so, client computer 10 will then obtain a new prescription number from the client, as represented by box 454. Otherwise, client computer 10 ends the telephone call, as represented by box 472.

When on-line communications are re-established and client computer 10 conducts validation processing, the refill requests that are determined to be valid are stored for dispense processing, and the refill requests that are determined to be invalid are stored for notification processing, as discussed below.

If client computer 10 determines, as represented by box 445 on FIG. 5*a*, that interactive communications with host computer 16 are available, then on-line communications processing is initiated, represented by box 476. Client computer 10 functions according to the on-line configuration and thus expects interactive on-line communications with host computer 16 to exist. Once engaged in on-line communications processing, client computer 10 collects specific request information from the patient, such as patient identification number, patient prescription number, or other information, represented by boxes 478 and 484 on FIG. 5*b*. Client computer 10 then validates the caller's request with the host computer, as represented by box 486. The caller is then informed of his or her validated refill status, as represented by box 487. Finally, client computer 10 queries the caller as to whether the caller has another refill request, as represented by box 496. If so, client computer 10 then obtains a new prescription number from the client, as represented by box 484. Otherwise, client computer 10 ends the telephone call, as represented by box 472.

Now referring to FIG. 5*c*, when the operator has configured client computer 10 for on-line communications with automatic validation processing, validation processing for client computer 10 is initiated, as represented by box 415. Client computer 10 performs off-line detection by using a verification transaction, a software method, or by monitoring statuses rendered from other communications-related hardware devices, as represented by box 488. The verification transaction determines, as represented by box 490, whether interactive communications with host computer 16 are available to perform inquiries.

If on-line communications with host computer 16 are not available, i.e., host computer 16 is off-line, the client computer software processing is continued, as represented by box 410.

If client computer 10 determines, as represented by box 490, that interactive communications with host computer 16 are available, then an inquiry transaction is initiated from client computer 10 to host computer 16, to determine whether any unvalidated requests are stored in data storage 14, as represented by box 493. If no unvalidated requests exist, the client computer software processing is continued, as represented by box 410.

If client computer 10 determines, as represented by box 492, that unvalidated requests are stored in data storage 14, then the unvalidated requests are retrieved and an inquiry transaction is initiated from client computer 10 to host computer 16, as represented by box 493.

Client computer 10 then determines, represented by box 494, whether the client request is a valid request. A request that is validated by host computer 16 is stored on client computer 10 for dispense transaction processing as a valid pending refill request, represented by box 495. Conversely, invalidated refill requests are stored on client computer 10 as invalid refill requests for notification or report processing, as represented by box 497. Valid refill requests are used in a dispense transaction to dispense the prescription refill on host computer 14. Invalid refill requests are stored for notification processing, as discussed below. After invalid refill requests are stored, as represented by box 497, client computer 10 then determines, as represented by box 492, whether any additional stored unvalidated requests exist.

Notification Processing

Once it is determined that the client computer 10 is not in communication with host computer 16 or the system is off-line, and requests for refills are received by client computer 10, the requests are stored for validation processing, as represented by boxes 160 of FIG. 1, 260 of FIG. 3*b*, and 460 of FIG. 5*b*.

Once on-line communication is re-established between client computer 10 and host computer 16, client computer 10 may then perform the validation processing task as represented by box 415 of FIG. 5*a* and shown in detail in FIG. 5*c*, boxes 415 through 497. At this point, the caller is unaware of whether his or her refill request has been determined to be valid or invalid. Therefore, in another embodiment of the invention, client computer 10 performs notification processing as represented in box 515 of FIG. 5a and FIG. 5d.

Notification processing may be a manual or automated process. Manual notification processing is accomplished by using client computer 10 to produce a readable report that can be used by a technician for notifying the patients or any other business use.

A human operator can issue a notify command that will cause client computer 10 to perform automated notification processing. Automated notification processing uses some or all of the existing telephone lines and attempts to contact all patients whose refill requests are found to be invalid. The notify command initiates the process that determines whether any invalid refill requests exist.

In the preferred embodiment, client computer 10 determines whether invalid refill requests exist. Client computer 10 then extracts the telephone number and status associated with the request and attempts to contact the patient. The automatic notification process only executes within specified hours. Therefore, calls are only placed during hours specified in this program, for example, during normal business hours or during home evening hours.

Client computer 10 attempts to call the patient on the telephone and inform the patient of the invalid refill status as determined during validation processing. In the event that a call is busy or unanswered, client computer 10 attempts another call at a later time until a defined period of time has elapsed or a total number of attempts has reached a defined limit. If the defined period of time or a total number of attempts has reached a defined limit, the invalid refill request status is stored for reporting as "not delivered". If a time period or predetermined retry count is reached, the invalid refill request status is stored for reporting as "not deliverable". If a telephone company situation information tone (SIT Tone) is received, then the invalid refill request is stored for reporting as "undeliverable". If the call is answered by an answering machine, methods known in the art are employed to attempt to leave a message stating the invalid status of the refill request. If the message is successfully delivered then the invalid refill request status is stored for reporting as "delivered". Finally, if a call is answered by a patient, a message stating the invalid status of the refill request is given to the patient with an option to repeat the message or to transfer to a technician. Additionally, other appropriate options may be given. If the message is delivered, then an invalid request status is stored for reporting as "delivered".

Whether the call was "not delivered," "delivered," or "undeliverable," the call disposition is stored. The call disposition reflects whether the call was busy, or if there was no answer, SIT tones, answering machine, a live patient, etc.

In the preferred embodiment, software processes run by client computer 10 have components that may perform report processing. Some reports are automatically generated and other reports may be generated as requested by an operator. A report may be produced in a computer readable format for use by another process or the report may be in a human readable form that could be used by a technician.

Client Computer Configured for On-Line Communications with Automatic Notification Processing Referring now to FIG. 5d, client computer 10 first determines whether the current time is within allowable calling hours as represented by box 525. If not, client computer 10 continues the software processing tasks as represented in box 410. If the current time is within allowable calling hours, then client computer 10 determines whether any stored invalid refill requests exist, as represented by box 535. If not, then client computer 10 continues software processing tasks as represented by box 410.

If stored invalid refill requests do exist, then client computer 10 obtains an invalid refill request from local database 14. Client computer 10 then extracts the original telephone number, original request time and validated status from the invalid request as represented in box 545. Client computer 10 then determines whether it is timely to deliver a notification message by assessing the elapsed time since a previous refill request was made, e.g., if a predetermined period of time has elapsed then no further notification messages will be issued. Client computer 10 preferably additionally determines whether a retry count is below an established limit, as represented by box 555.

If it is determined that the notification message is untimely or a retry count is above an acceptable limit, then a message delivery counter is incremented and the refill request is assigned a "not deliverable" message status for report processing as represented by 595. If the notification message is determined to be timely and the retry count is below an acceptable limit as represented by box 555, then client computer 10 performs a notification telephone call function by attempting delivery of an invalid request message to the patient as represented by box 565. Examples of invalid request messages include: "This prescription is expired"; "This prescription is discontinued"; "It is too early to fill this prescription. Please call back after 'an appropriate date'"; "No refills are available"; "This prescription cannot be filled"; or other appropriate messages. The notification telephone call function is represented by box 565 and described in greater detail below, and is represented in greater detail by boxes 610 through 687 in FIG. 5e. Box 565 also appears as "enter" and "exit" boxes in FIG. 5e to illustrate that boxes 610 through 687 represent box 565 in greater detail.

Referring back to FIG. 5d, the process for performing client computer notification processing is set forth. Client computer 10 then determines whether the notification message was delivered, as represented by box 575.

If client computer 10 determines that the notification message was delivered, as represented by box 575, then client computer 10 increments a message delivery attempt counter and stores a delivered message status for report processing, as represented by box 580. Client computer 10 then continues client computer software processing tasks as represented by box 410.

If client computer 10 determines that the notification message is deliverable, as represented by box 585, then client computer 10 increments the message delivery attempt counter and stores "not delivered" message status for report processing and stores the invalid request for future retrieval by client computer 10 in future attempts at notification as represented by box 590. Client computer 10 then continues software processing tasks as represented by box 410.

If the notification message was determined by client computer 10 to have not been delivered, as represented by box 575, then client computer 10 determines whether the notification message was deliverable as represented by box 585. A preferred method of determining whether a message was deliverable is made by at least one of the series of tests represented by boxes 630 through 680 in FIG. 5e. If client computer 10 determines that the notification message is not deliverable, as represented by box 585, then client computer 10 increments the message delivery counter and stores a "not deliverable" message status for report processing, as represented by box 595.

The notification telephone call function and determination of whether a message is "deliverable", as represented by boxes 565, 575 and 585 in FIG. 5d, is shown in greater detail in FIG. 5e. To perform the notification telephone call function represented by box 565 in FIG. 5d, the client computer 10 first determines whether a telephone line is available as represented by box 610 in FIG. 5e. If a telephone line is determined to not be available, then client computer 10 determines that the notification message was "not delivered", as represented by box 617 in FIG. 5e. Call progress status, such as "not delivered" status, is assigned to the refill request. If client computer 10 determines that the telephone line is available, as represented by box 610, then client computer 10 dials the patient's telephone number as represented by box 620. Client computer 10 then determines whether the answering party is a human patient as represented by box 630. If the answering patient is a human party, then the client computer plays an "invalid refill request notification" message to the patient, as represented in box 633.

In the preferred embodiment, client computer 10 allows the answering party to transfer to personnel, to repeat the message, or to engage other options, as represented by box 635. Client computer 10 then indicates that the message was delivered, as represented by box 637 and returns to the notification process as represented by "exit" box 565 in FIG. 5e.

If client computer 10 determines that a human patient has not answered the phone, as represented by box 630, client computer 10 then determines whether an electronic answering device has answered the phone, as known in the art, and represented by box 640. If it is determined that an electronic answering device has answered the phone, as represented by box 640, then client computer 10 plays an "invalid refill request" notification message to be recorded by the answering device as indicated by box 643. Client computer 10 then indicates that the message was delivered as indicated by box 647 and returns to the notification process as indicated by box 565 in FIG. 5e.

If client computer 10 determines that an electronic answering device has not answered the phone, as represented by box 640, then client computer 10 checks to determine if the line is busy as indicated by box 650. If it is determined that the line is busy, then client computer 10 indicates that the message was not delivered, as indicated in box 657. Client computer 10 then returns to the notification process, as indicated in box 565 in FIG. 5e.

If client computer 10 determines that there was no busy signal, as represented by box 650, then client computer 10 checks to determine whether there is a ring with no answer, as represented by box 660. If it is determined by the test represented by box 660 that there is a ring and no answer, then client computer 10 indicates that the message was not delivered, as indicated by box 657, and returns to the notification process as represented in box 565 in FIG. 5e.

If client computer 10 determines that it is not the case that there is a ring with no answer as indicated by box 660, then client computer 10 checks to determine whether there is no ring back as indicated in box 670. If there is no ring back, then client computer 10 indicates that the message was not delivered as represented by box 657 and returns to notification process as represented by box 565 in FIG. 5e.

If it is not the case that there is no ring back as indicated in box 670, then client computer 10 determines whether there is a situation information tone (SIT tone) as indicated in box 680. If there is a SIT tone, client computer 10 then indicates that the message was undeliverable, as represented in box 687. Client computer 10 then returns the call progress status to the notification process as indicated by boxes 687 and 565 in FIG. 5e.

Similarly, if there is no situation information tone, the message is still determined to be undeliverable since previous tests indicate that the message is undeliverable, as represented by boxes 630, 640, 650, 660 and 670. Therefore, client computer 10 determines that the message is undeliverable and returns the call progress status to a notification process as indicated in boxes 687 and 565 in FIG. 5e.

Figure 6A:
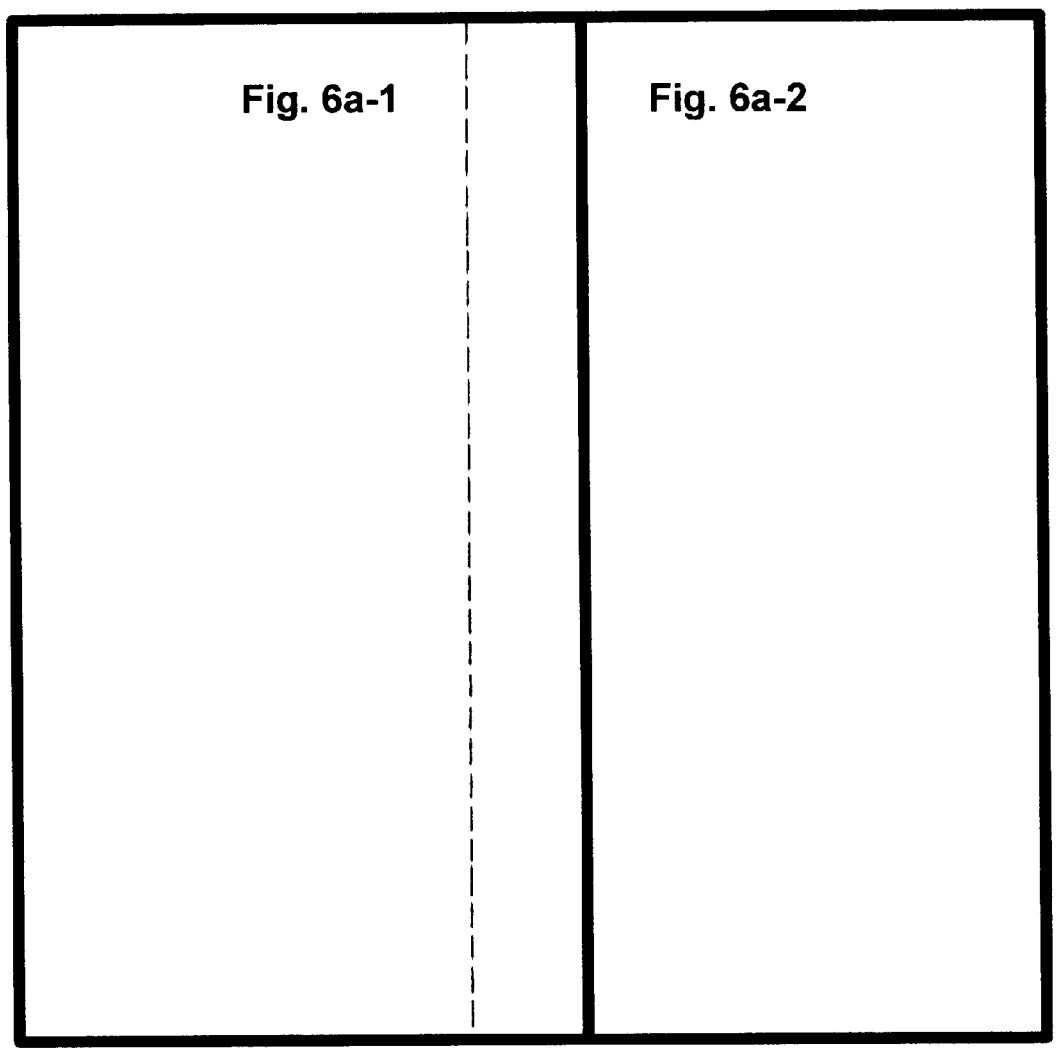
FIGS. 6a and 6b are flow diagrams depicting the on-line or off-line communications configuration of the client computer with manual notification processing.
Figures 1, 6A:
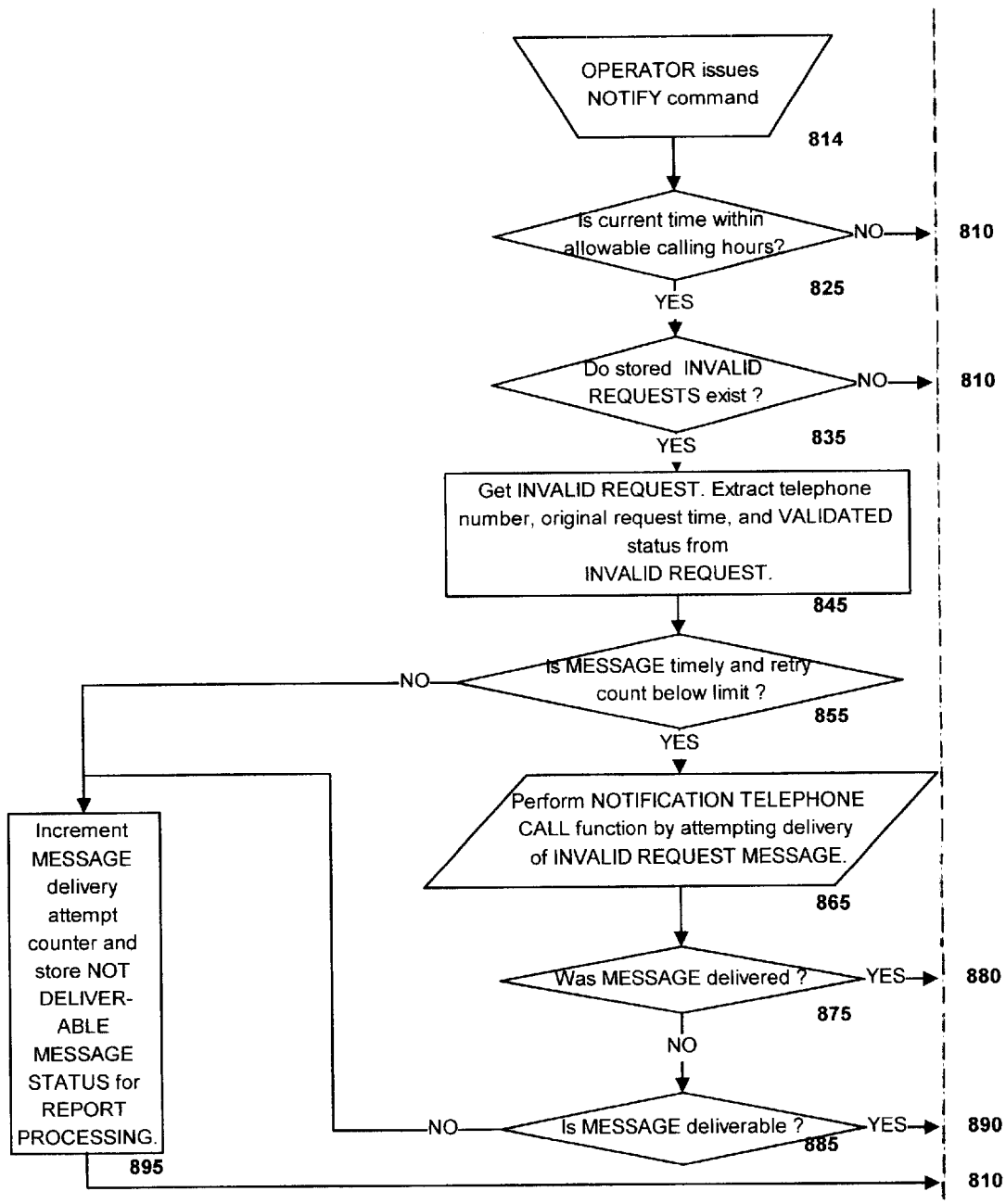
Figures 2, 6A:
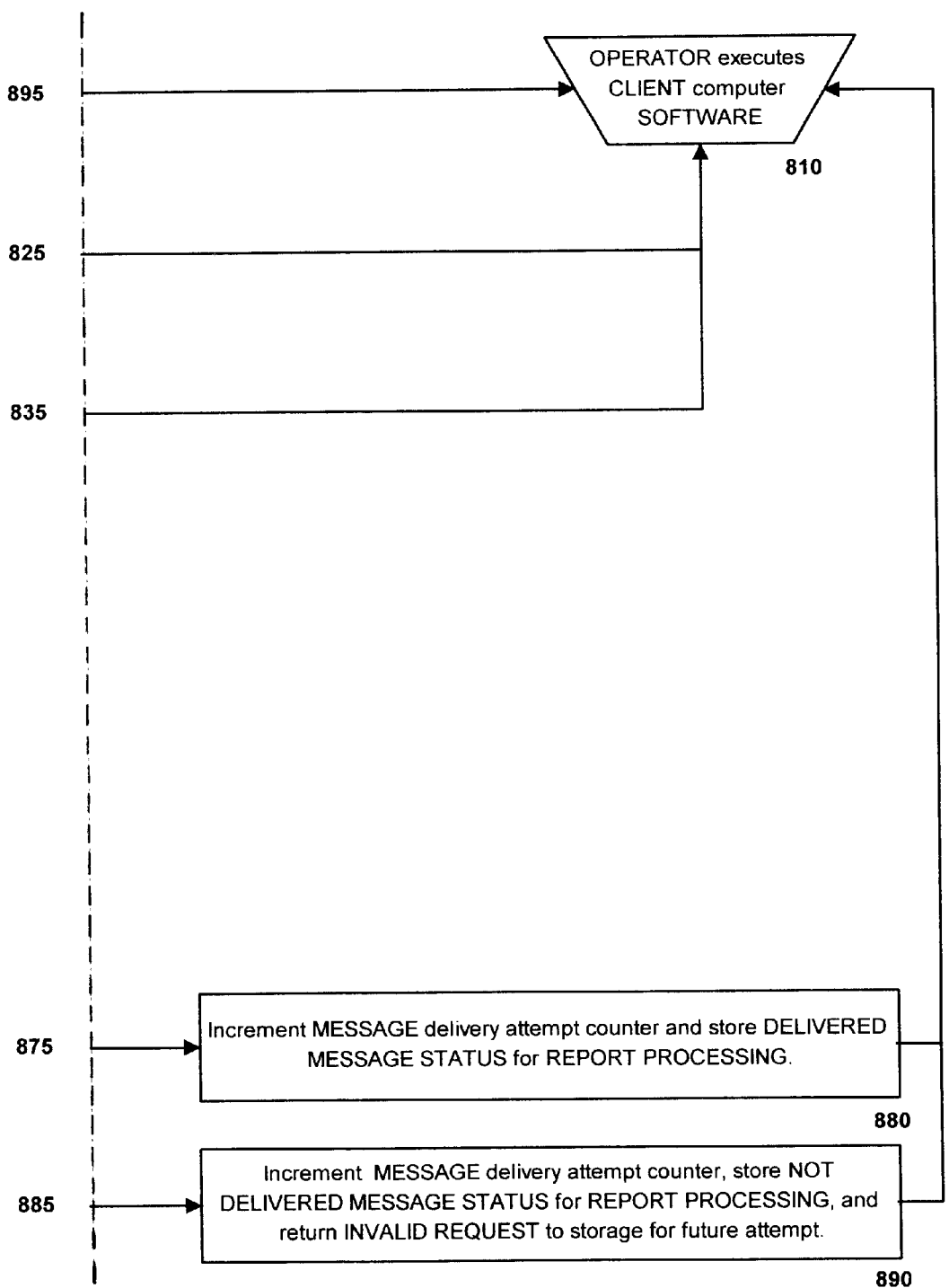

Client Computer Configured for On-Line or Off-Line Communications Using Manual Notification Referring now to FIG. 6a, an operator issues a NOTIFY command, as indicated by box 814. Client computer 10 then determines whether the current time is within allowable calling hours as represented by box 825. If not, client computer 10 continues the software processing tasks as represented in box 810. If the current time is within allowable calling hours, then client computer 10 determines whether any stored invalid refill requests exist, as represented by box 835. If not, then client computer 10 continues software processing tasks as represented by box 810.

If stored invalid refill requests do exist, then client computer 10 obtains an invalid refill request from local database 14. Client computer 10 then extracts the original telephone number, original request time and validated status from the invalid request as represented in box 845. Client computer 10 then determines whether it is timely to deliver a notification message by assessing the elapsed time since a previous refill request was made, e.g., if a predetermined period of time has elapsed, then no further notification message will be issued. Client computer 10 additionally determines whether a retry count is below an established limit, as represented by box 855.

If it is determined that the notification message is untimely or a retry count is above an acceptable limit, then a message delivery counter is incremented and the refill request is assigned a "not deliverable" message status for report processing as represented by 895. If the notification message is determined to be timely and the retry count is below an acceptable limit as represented by box 855, then client computer 10 performs a notification telephone call function by attempting delivery of an invalid request message to the patient as represented by box 865. The notification telephone call function represented by box 865 and described in greater detail below, is represented in greater detail by boxes 910 through 987 in FIG. 6b. Box 865 also appears as "enter" and "exit" boxes in FIG. 5e to illustrate that boxes 610 through 687 represent box 565 in greater detail.

Referring back to FIG. 6a, the process for performing manual client computer notification processing is set forth. Client computer 10 then determines whether the notification message was delivered, as represented by box 875.

If client computer 10 determines that the notification message was delivered, as represented by box 875, then client computer 10 increments a message delivery attempt counter and stores a delivered message status for report processing, as represented by box 880. Client computer 10 then continues client computer software processing tasks as represented by box 810.

If client computer 10 determines that the notification message is deliverable, as represented by box 885, then client computer 10 increments the message delivery attempt counter and stores "not delivered" message status for report processing and stores the invalid request for future retrieval by client computer 10 in future attempts at notification as represented by box 890. Client computer 10 then continues software processing tasks as represented by box 810.

If the notification message was determined by client computer 10 to have not been delivered, as represented by box 875, then client computer 10 determines whether the notification message was deliverable as represented by box 885. A preferred method of determining whether a message was deliverable is made by at least one of the series of tests represented by boxes 930 through 980 in FIG. 6*b*. If client computer 10 determines that the notification message is not deliverable, as represented by box 885, then client computer 10 increments the message delivery counter and stores a "not deliverable" message status for report processing, as represented by box 895.

Figure 6B:
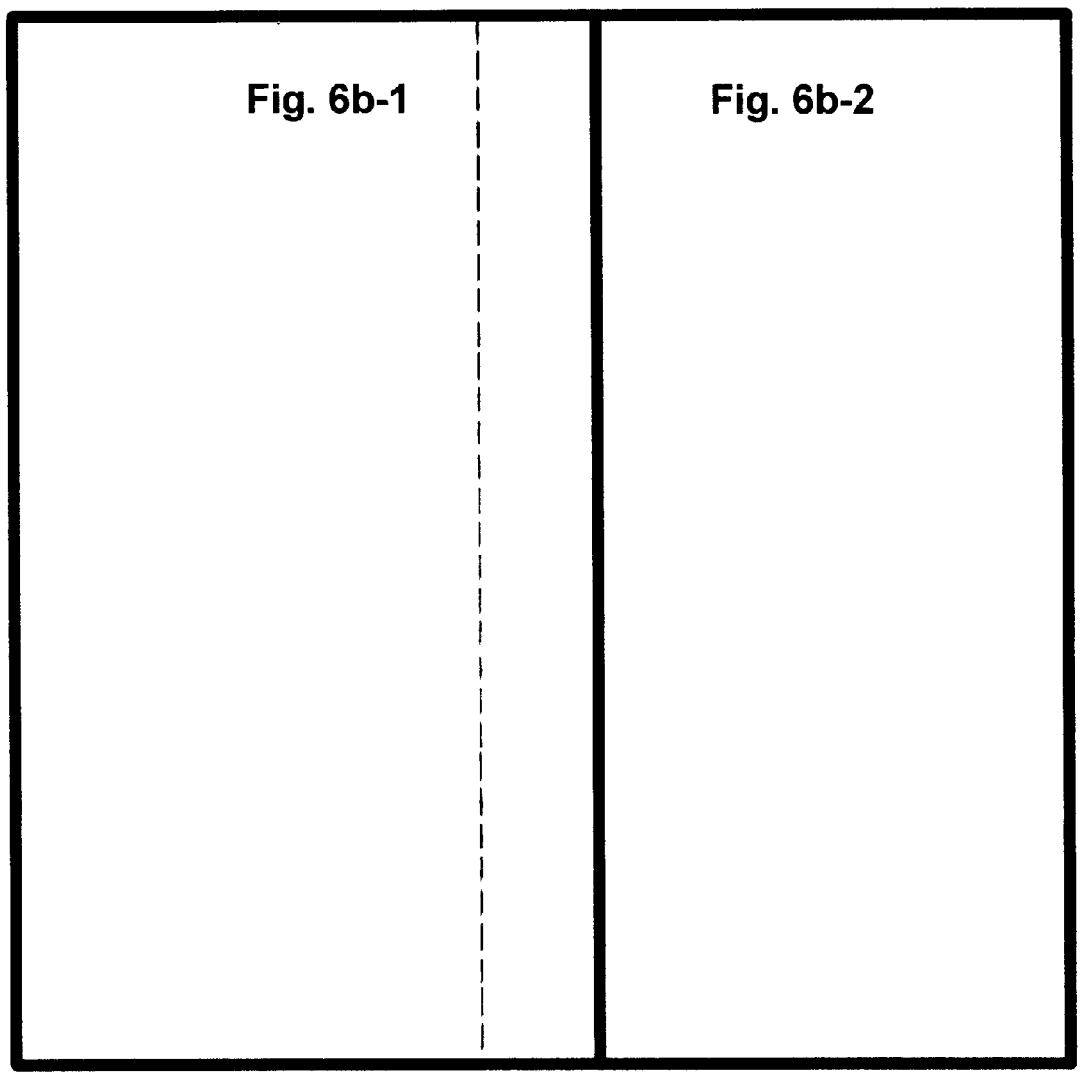
Figures 1, 6B:
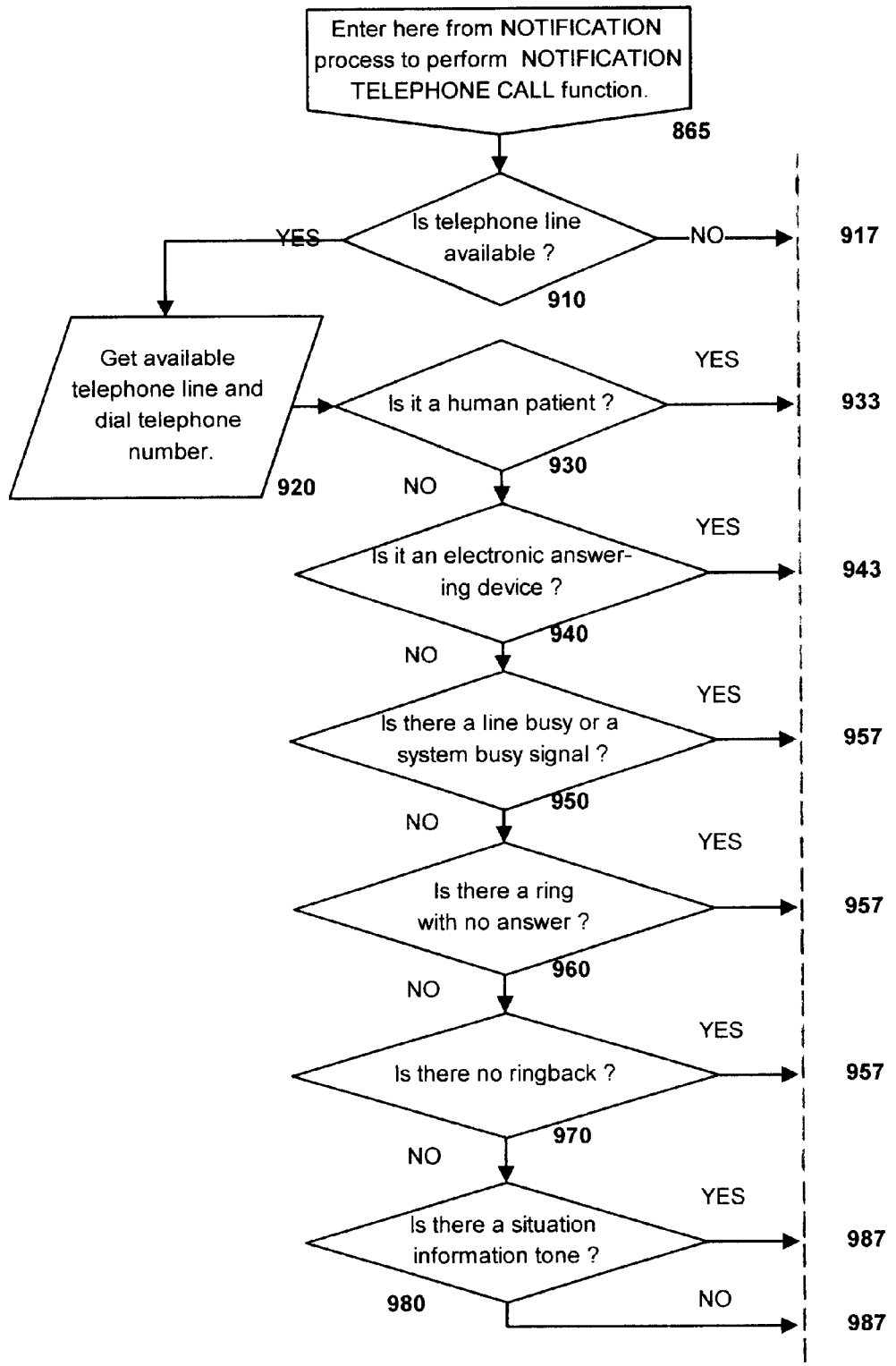
Figures 2, 6B:
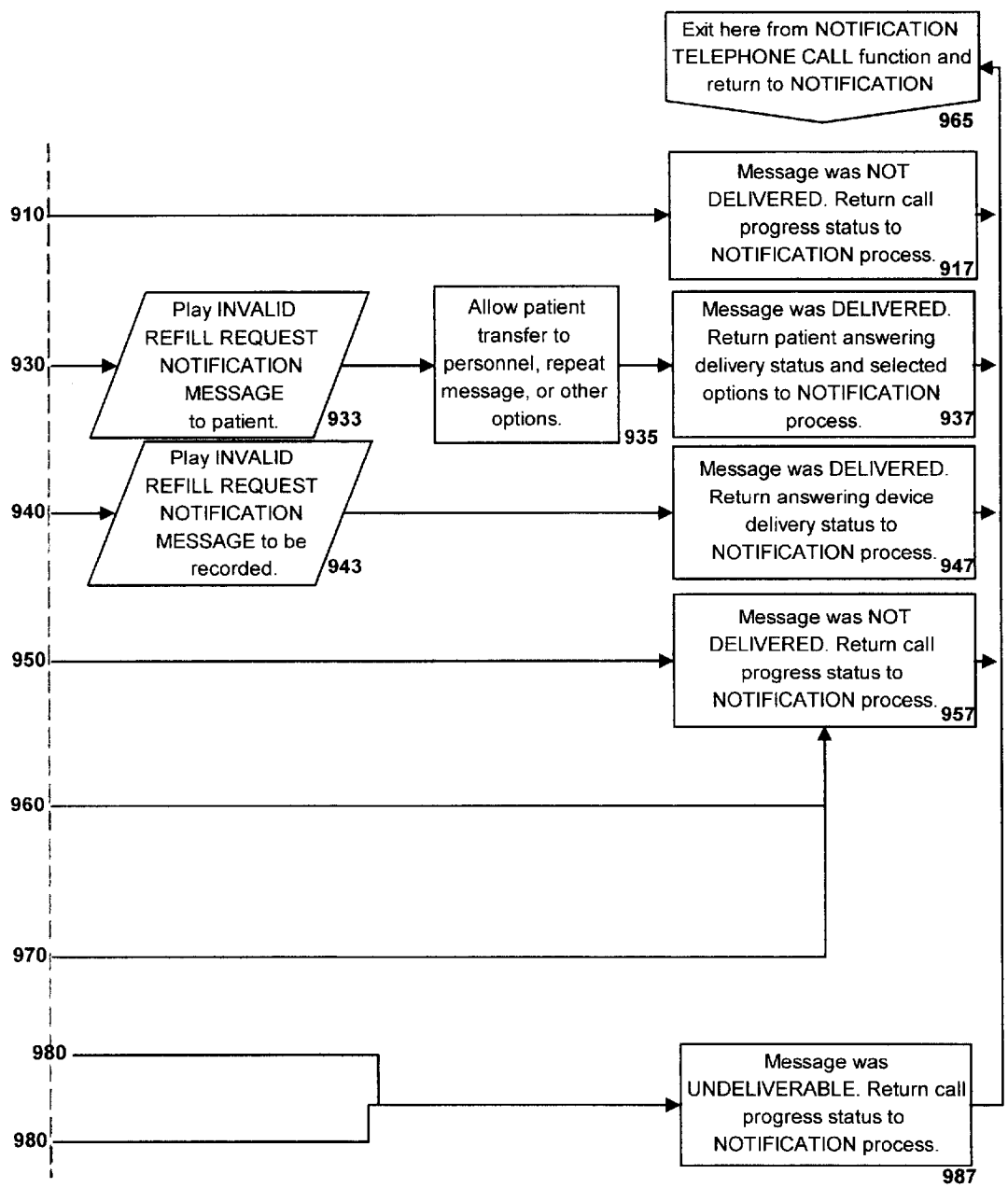

Referring now to FIG. 6*b*, the notification telephone call function and determination of whether a message is "deliverable", as represented by boxes 865, 875 and 885 in FIG. 6*a*, is shown in greater detail. To perform the notification telephone call function represented by box 865 in FIG. 6*a*, the client computer 10 first determines whether a telephone line is available as represented by box 910, as shown in FIG. 6*b*. If a telephone line is determined lo to not be available, then client computer 10 determines that the notification message was "not delivered", as represented by box 917, as shown in FIG. 6*b*. Call progress status, such as "not delivered" status, is assigned to the refill request. If client computer 10 determines that the telephone line is available, as represented by box 910, then client computer 10 dials the patient's telephone number as represented by box 920. Client computer 10 then determines whether the answering party is a human patient as represented by box 930. If the answering party is a human party, then the client computer plays an "invalid refill request notification" message to the patient, as represented in box 933.

In the preferred embodiment, client computer 10 allows the answering party to transfer to personnel, to repeat the message, or to engage other options, as represented by box 935. Client computer 10 then indicates that the message was delivered, as represented by box 937 and returns to the notification process as represented by box 865.

If client computer 10 determines that a human patient has not answered the phone, as represented by box 930, client computer 10 then determines whether an electronic answering device has answered the phone, as known in the art, and represented by box 940. If it is determined that an electronic answering device has answered the phone, as represented by box 940, then client computer 10 plays an "invalid refill request" notification message to be recorded by the answering device as indicated by box 943. Client computer 10 then indicates that the message was delivered as indicated by box 947 and returns to the notification process as indicated by box 865.

If client computer 10 determines that an electronic answering device has not answered the phone, as represented by box 940, then client computer 10 checks to determine if the line is busy as indicated by box 950. If it is determined that the line is busy, then client computer 10 indicates that the message was not delivered, as indicated in box 957. Client computer 10 then returns to the notification process, as indicated in "exit" box 865 in FIG. 6*b*.

If client computer 10 determines that there was no busy signal, as represented by box 950, then client computer 10 checks to determine whether there is a ring with no answer, as represented by box 960. If it is determined by box 960 that there is a ring and no answer, then client computer 10 indicates that the message was not delivered, as indicated by box 957, and returns to the notification process as represented in box 865 in FIG. 6*b*.

If client computer 10 determines that it is not the case that there is a ring with no answer as indicated by box 960, then client computer 10 checks to determine whether there is no ring back as indicated in box 970. If there is no ring back, then client computer 10 indicates that the message was not delivered as represented by box 957 and returns to the notification process as represented by box 865 in FIG. 6*b*.

If it is not the case that there is no ring back as indicated in box 970, then client computer 10 determines whether there is a situation information tone (SIT tone) as indicated in box 980. If there is a SIT tone, client computer 10 then indicates that the message was undeliverable, as represented in box 987. Client computer 10 then returns the call progress status to the notification process as indicated by boxes 987 and 865 in FIG. 6*b*. Similarly, if there is no situation information tone, the message is still determined to be undeliverable since previous tests indicate that the message is undeliverable, as represented by boxes 930, 940, 950, 960 and 970. Therefore, client computer 10 determines that the message is undeliverable and returns the call progress status to a notification process as indicated in boxes 987 and 865 in FIG. 6*b*.

Whereas, the present invention has been described in relation to the drawings attached hereto, it should be understood that other and further modifications, apart from those shown or suggested herein, may be made within the spirit and scope of this invention.

What is claimed is:

1. A method for processing requests for prescription refills between one or more client computers and a host computer, comprising the steps of:

receiving a request for a prescription refill from a caller, said receiving of said request being facilitated by a client computer;

storing said request until on-line communications with a host computer are established, said storing of said request being facilitated by a first client computer storage means;

establishing a communication link between said client computer and said host computer, said establishing of said communication link being facilitated by a communication network; and processing said request between said client computer and said host computer, said processing of said request being facilitated first client computer code segment and a first host code segment.

2. The method of claim 1, wherein said step of receiving a request is further defined as:

answering an incoming telephone call from a caller, said answering of said incoming telephone call being facilitated by a client computer; and receiving a request for a prescription refill from said caller.

3. The method of claim 1, wherein said step of processing said request is further defined as:

attempting to validate said request by comparing said request with patient information stored in a patient information databank; and if said request is a valid request, processing said valid request for dispensing, said processing of said valid request being facilitated by a dispensing transaction process.

4. The method of claim 3, wherein said patient information databank is stored within said client computer and said step of validating is preformed when communications between said client computer and said host computer are off-line.

5. The method of claim 3, wherein said patient information databank is stored within said host computer and said step of validating is preformed when communications between said client computer and said host computer are on-line.

6. The method of claim 3, further comprising a step of storing said validated request for dispense processing, said storing of said validated request being facilitated by a client computer storage means.

7. The method of claim 3, further comprising the step of storing said invalidated requests for notification processing, said storing of said validated request being facilitated by a client computer storage means.

8. A computer program embodied on computer-readable medium having a computer readable program code embodied in said medium for effecting a method of processing requests for prescription refills between at least one client computer and a host computer, comprising:

a code segment for receiving a request for a prescription refill from a caller;

a code segment for storing said request until on-line communications with a host computer is established;

a code segment for establishing a communication link between said client computer and said host computer; and a code segment for processing said request between said client computer and said host computer.

9. The computer of claim 8, wherein said a code segment for receiving said request is further defined as:

a code segment for answering an incoming telephone call from a caller; and a code segment for receiving an audible request for a prescription refill from said caller.

10. The computer of claim 8, wherein said a code segment for receiving said request is further defined as:

a code segment for attempting to validate said request by comparing said request with patient information stored in a patient information databank; and if said request is a valid request, a code segment for processing said valid request for dispensing.

11. The computer of claim 8, further comprising:

a code segment for storing said patient information databank within said client computer; and a code segment for causing said attempt to validate said request between said client computer and said host computer to be facilitated when communications are off-line.

12. The computer of claim 8, further comprising:

a code segment for storing said patient information databank within said client computer; and a code segment for causing said attempt to validate said request between said client computer and said host computer to be facilitated when communications are on-line.

13. The computer of claim 8, further comprising a code segment for storing within said client computer said validated request for dispense processing.

14. The computer of claim 8, further comprising a code segment for storing within said client computer said invalidated requests for notification processing.

* * * * *